US012603154B2

(12) United States Patent
Beal et al.

(10) Patent No.: US 12,603,154 B2
(45) Date of Patent: Apr. 14, 2026

(54) FAST-NA FOR THREAT DETECTION IN HIGH-THROUGHPUT SEQUENCING

(71) Applicant: RTX BBN Technologies, Inc., Cambridge, MA (US)

(72) Inventors: Jacob Stuart Michael Beal, Iowa City, IA (US); Thomas Cushing Mitchell, Boston, MA (US); Daniel Wyschogrod, Newton, MA (US)

(73) Assignee: RTX BBN Technologies, Inc., Cambridge, MA (US)

( * ) Notice: Subject to any disclaimer, the term of this patent is extended or adjusted under 35 U.S.C. 154(b) by 828 days.

(21) Appl. No.: 17/181,865

(22) Filed: Feb. 22, 2021

(65) Prior Publication Data

US 2021/0335452 A1 Oct. 28, 2021

Related U.S. Application Data

(60) Provisional application No. 63/013,875, filed on Apr. 22, 2020, provisional application No. 63/013,872, filed on Apr. 22, 2020.

(51) Int. Cl.
| | |
|---|---|
| *G16B 40/00* | (2019.01) |
| *G16B 30/00* | (2019.01) |
| *G16B 30/10* | (2019.01) |
| *G16B 45/00* | (2019.01) |
| *G16B 50/00* | (2019.01) |

(52) U.S. Cl.
CPC .............. *G16B 40/00* (2019.02); *G16B 30/00* (2019.02); *G16B 30/10* (2019.02); *G16B 45/00* (2019.02); *G16B 50/00* (2019.02)

(58) Field of Classification Search
CPC ........ G16B 40/00; G16B 30/00; G16B 30/10; G16B 45/00; G16B 50/00
See application file for complete search history.

(56) References Cited

U.S. PATENT DOCUMENTS

| | | |
|---|---|---|
| 2005/0050101 A1 | 3/2005 | Vockley et al. |
| 2016/0132640 A1* | 5/2016 | Layer ..................... G16B 20/20 |
| | | 706/12 |
| 2018/0089365 A1 | 3/2018 | Beal et al. |
| 2021/0335454 A1 | 10/2021 | Beal et al. |

OTHER PUBLICATIONS

Chen, Shifu, et al. "AfterQC: automatic filtering, trimming, error removing and quality control for fastq data." BMC bioinformatics 18.3 (2017): 91-100. (Year: 2017).*
Bradley P. Ultrafast search of all deposited bacterial and viral genomic data. Nature Biotechnology 37: 152-159. (Year: 2019).*
Kovaka S. Targeted nanopore sequencing by real-time mapping of raw electrical signal with UNCALLED. BioRxiv 931923, 36 pgs. (Year: 2020).*

Kar et al. (2019). That's My DNA: Detecting Malicious Tampering of Synthesized DNA. In: Foley, S. (eds) Data and Applications Security and Privacy XXXI II. DBSec 2019. Lecture Notes in Computer Science(), vol. 11559. Springer, Cham. (Year: 2019).
Pearson, William. An introduction to sequence similarity ("Homology") searching, Curr. Protoc. Bioinform.42:3.1.1-3.1.8.C© 2013 by John Wiley & Sons, Inc. (Year: 2013).
Wyschogrod, D., et al., "False alarm reduction in automatic signature generation for zero-day attacks," Proceedings of the Second Cyberspace Research Workshop, Shreveport, Louisiana, (2009), pp. 73-81.
Wyschogrod, D., et al., "Using automatic signature generation as a sensor backend", Proceedings of CSIIRW09, Oak Ridge, Tennessee, (2009).
Fredericks, D.N., et al., "Sequence-based identification of microbial pathogens: a reconsideration of Koch's postulates," Clinical Microbiology Reviews, vol. 9, No. 1, (1996), pp. 18-33.
Melsted, P., et al., "Efficient counting of k-mers in DNA sequences using a bloom filter." BMC Bioinformatics, 12:333, (2011), pp. 1-7.
Barczak, A. K., et al., "RNA signatures allow rapid identification of pathogens and antibiotic susceptibilities," Proceedings of the National Academy of Sciences, vol. 109, No. 16, (2012), pp. 6217-6222.
International Search Report and Written Opinion in International Patent Application No. PCT/US2021/019077 dated Jun. 4, 2021.
Beal, J., et al., "Highly distinguished amino acid sequences of 2019-nCoV (Wuhan Coronavirus)," bioRxiv, (2020).
Adali, S.S., et al., "Towards detection of engineering in metagenomic sequencing data for yeast and other fungi," International Workshop on Biodesign Automation, (2019), pp. 28-29.
International Search Report and Written Opinion in International Patent Application No. PCT/US2021/019082 dated Jun. 10, 2021.
Bloom, Burton H., "Space/Time Trade-offs in Hash Coding with Allowable Errors", Communications of the ACM, vol. 13, No. 7, Jul. 1970, pp. 422-426.

(Continued)

*Primary Examiner* — Olivia M. Wise
*Assistant Examiner* — Robert J. Kallal
(74) *Attorney, Agent, or Firm* — Schwegman Lundberg & Woessner, P.A.

(57) ABSTRACT

According to an example, a method of analyzing an output of a sequencer is provided comprising identifying genetic targets, obtaining target signature snippets responsive thereto, each target signature snippet derived from a genetic sequence of the genetic targets, receiving portions of a test sequence output by a sequencer sequencing a sample in real time, determining, in real time or near-real time with the sequencer sequencing the sample, whether a target signature snippet of the target signature snippets is in at least one portion of the test sequence, determining, for each genetic target, a probability the genetic target is in the sample based on the determination of whether the target signature snippet is present in the at least one portion of the test sequence, and outputting an analysis of the sample indicating the respective probability that each genetic target is present in the sample.

20 Claims, 12 Drawing Sheets

(56)　　　　　References Cited

OTHER PUBLICATIONS

Elhefnawi et al., "Identification of novel conserved functional motifs across most Influenza A viral strains", Virology Journal 2011, pp. 1-10.

Luscombe et al., "The dominance of the population by a selected few: power-law behaviour applies to a wide variety of genomic properties", Genome Biology, 2002, pp. 1-7.

Mantegna et al., "Systematic analysis of coding and noncoding DNA sequences using methods of statistical linguistics", Physical Review E, vol. 52, No. 3, Sep. 1995, pp. 2939-2950.

Qian, et al., "Protein Family and Fold Occurrence in Genomes: Power-law Behaviour and Evolutionary Model", Journal of Molecular Biology, 2001, pp. 673-681.

Shendure et al., "Next-generation DNA sequencing", Nature Biotechnology 26, 2008, pp. 1135-1145.

"U.S. Appl. No. 17/181,858, Advisory Action mailed Sep. 25, 2024", 4 pgs.

"U.S. Appl. No. 17/181,858, Appeal Decision mailed Jan. 3, 2024", 2 pgs.

"U.S. Appl. No. 17/181,858, Examiner Interview Summary mailed Jun. 8, 2023", 3 pgs.

"U.S. Appl. No. 17/181,858, Examiner Interview Summary mailed Aug. 13, 2024", 2 pgs.

"U.S. Appl. No. 17/181,858, Final Office Action mailed Jul. 15, 2024", 15 pgs.

"U.S. Appl. No. 17/181,858, Final Office Action mailed Sep. 14, 2023", 25 pgs.

"U.S. Appl. No. 17/181,858, Non Final Office Action mailed Feb. 7, 2024", 26 pgs.

"U.S. Appl. No. 17/181,858, Non Final Office Action mailed Mar. 30, 2023", 16 pgs.

"U.S. Appl. No. 17/181,858, Non Final Office Action mailed Apr. 17, 2025", 24 pgs.

"U.S. Appl. No. 17/181,858, Pre-Appeal Brief Request filed Dec. 12, 2023", 5 pgs.

"U.S. Appl. No. 17/181,858, Response filed Apr. 4, 2024 to Non Final Office Action mailed Feb. 7, 2024", 11 pgs.

"U.S. Appl. No. 17/181,858, Response filed Jun. 21, 2023 to Non Final Office Action mailed Mar. 30, 2023", 14 pgs.

"U.S. Appl. No. 17/181,858, Response filed Aug. 18, 2025 to Non Final Office Action mailed Apr. 17, 2025", 20 pgs.

"U.S. Appl. No. 17/181,858, Response filed Sep. 12, 2024 to Final Office Action mailed Jul. 15, 2024", 10 pgs.

"European Application Serial No. 21712339.7, Communication Pursuant to Article 94(3) EPC mailed Sep. 26, 2024", 6 pgs.

"European Application Serial No. 21712622.6, Communication Pursuant to Article 94(3) mailed Aug. 9, 2024", 9 pgs.

"International Application Serial No. PCT/US2021/019077, International Preliminary Report on Patentability mailed Nov. 3, 2022", 8 pgs.

"International Application Serial No. PCT/US2021/019082, International Preliminary Report on Patentability mailed Nov. 3, 2022", 9 pgs.

"Korean Application Serial No. 10-2022-7031890, Notice of Preliminary Rejection mailed Jun. 19, 2025", w/ English translation, 10 pgs.

"Korean Application Serial No. 10-2022-7031890, Response filed Aug. 22, 2025 to Notice of Preliminary Rejection mailed Jun. 19, 2025", W/ English Claims, 29 pgs.

"Korean Application Serial No. 10-2022-7031892, Notice of Preliminary Rejection mailed Jun. 19, 2025", w/ English translation, 11 pgs.

"Korean Application Serial No. 10-2022-7031892, Response filed Aug. 22, 2025 to Notice of Preliminary Rejection mailed Jun. 19, 2025", W/English Claims, 27 pgs.

Sanderson, N D, et al., "Real-time analysis of nanopore-based metagenomic sequencing from infected orthopaedic devices", BMC Genomics, 19:714, (Sep. 27, 2018), 11 pgs.

Edwards, Robert A, et al., "Real Time Metagenomics: Using k-mers to annotate metagenomes", vol. 28 No. 24, pp. 3316-3317, (2012), 2 pgs.

Greninger, Alexander L, et al., "Rapid metagenomic identification of viral pathogensclinical samples by real-time nanopore sequencing analysis", Genome Medicine, 7:99, (Sep. 29, 2015), 13 pgs.

Loose, Matthew, et al., "Real-time selective sequencing using nanopore technology", Nature Methods, vol. 13, (2016), 751-754.

Stewart, Robert D, et al., "poRe GUIs for parallel and real-time processing of MinION sequence data", Sequence analysis, Bioinformatics, 33(14), pp. 2207-2208, (Jul. 15, 2017), 2 pgs.

Tausch, Simon H, et al., "LiveKraken-real-time metagenomic classification of illumina data", Bioinformatics, 34(21), pp. 3750-3752, (2018), 3 pgs.

* cited by examiner

310 Begin 320 identify plurality of benign snippets from first sequence 330 extract plurality of candidate signature snippets from second sequence 340 determine, for each of plurality of candidate signature snippets, whether it matches at least one of plurality of benign snippets 350 if no match, identify candidate signature snippet as malicious signature snippet 360 End

300

410 Begin 420 determine if malicious snippet is present in at least one test sequence 430 make determination about the at least one test sequence 440 End

400

710 Begin 720 determine if malicious snippet is present in at least one test sequence 730 make determination about the at least one test sequence 740 End

700

1100

1102
Begin

1104
Identify Group of Targets

1106
Obtain Target Signature Snippets for Each Target

1108
Receive Portion of Test Sequence

1110
Filter Portion of Test Sequence

1112
Identify Target(s) in Portion of Filtered Test Sequence

1114
End of Test Sequence?

NO

YES

1116
Determine Probability of Target Presence in Test Sequence

1118
Output Probability of Target Presence in Test Sequence

1120
End

FAST-NA FOR THREAT DETECTION IN HIGH-THROUGHPUT SEQUENCING

CROSS REFERENCE TO RELATED APPLICATIONS

This application claims priority under 35 U.S.C. § 119(e) to U.S. Provisional Application Ser. No. 63/013,872, titled "FAST-NA FOR DETECTION AND DIAGNOSTIC TARGETING," filed Apr. 22, 2020, and to U.S. Provisional Application Ser. No. 63/013,875, titled "FAST-NA FOR THREAT DETECTION IN HIGH-THROUGHPUT SEQUENCING," filed Apr. 22, 2020, each of which is incorporated herein by reference in its entirety.

STATEMENT REGARDING FEDERALLY SPONSORED RESEARCH OR DEVELOPMENT

This invention was made with government support under Contract No. W911NF-17-2-0092 awarded by the Intelligence Advanced Research Projects Activity (IARPA). The U.S. government has certain rights in this invention.

BACKGROUND

Technical Field

The application generally relates to detecting specific genetic sequences, and more particularly, in one aspect, to systems and methods for using sequence filters to identify and/or categorize snippets of malicious genetic sequences.

Background

Laboratories are currently able to manufacture deoxyribonucleic acid (DNA) and other sequences using nucleic acid sequence information. In an example scenario, a customer provides a laboratory with the nucleotides in a genetic sequence—in a format as simple as an electronic text file—and the laboratory synthesizes (i.e., manufactures) the sequence for delivery to the customer. This technology raises the specter of bad actors surreptitiously requesting the synthesis of malicious organisms. Diseases like influenza or anthrax could effectively be "mail ordered", thereby posing a public health risk. To prevent such a scenario, laboratories offering such synthesis services typically examine the genetic sequences provided by customers to ensure that the sequence is not associated with a malicious organism.

Current techniques are capable of recognizing sequences as short as approximately 200 base pairs. Yet recent advances in oligo-based assembly and editing, such as Clustered Regularly Interspaced Short Palindromic Repeat (CRISPR) mechanisms, allow for "clipping and stitching" small segments of DNA together. Unscrupulous customers could therefore avoid being detected by embedding parts of malicious organisms in the DNA sequences of multiple benign organisms, or by otherwise synthesizing malicious organisms in small fragments. The pathogenic sequences from these short or hybrid DNA sequences could then be reassembled into a malicious organism after they are synthesized and delivered.

A sample of genetic material may include a wide variety of genetic material, including pathogenic genetic material. A sample can be analyzed to identify one or more pathogens that are present in the sample. For example, a sample may be analyzed to determine whether a pathogen of interest is present in the sample. Samples may be sequenced by "sequencers" configured to analyze a sample and output information indicative of a genetic sequence of the sample. The genetic sequence may be analyzed to determine whether a pathogen of interest is present in the sample.

SUMMARY

Aspects and embodiments are directed to apparatus and methods for identifying target-organism "signatures"—relatively short snippets of genetic sequences that occur in target organisms but do not occur in similar but non-target organisms. What is considered a "target organism," and what distinguishes a target organism from a "non-target organism," may be controlled or selected by a user. For example, a target organism may be a malicious organism, such as the SARS-CoV-2 coronavirus, and non-target organisms may be benign organisms, such as other, non-malicious coronaviruses. In other examples, a target-organism signature may more broadly refer to a signature of any target organism for which it may be desirable to distinguish from non-target organisms. That is, while a target organism may be a malicious organism, it is to be appreciated that the phrase "target organism" is broader than malicious organisms. For example, a target organism may be an organism belonging to a particular species, genus, or other biological classification, and a non-target organism may be an organism not belonging to that particular biological classification. Other examples of target criteria are also within the scope of the disclosure. In various examples, a target organism or target genetic sequence may alternately or additionally be referred to as a "genetic sequence of interest," or "pathogen of interest," regardless of how the sequence or pathogen is otherwise classified, such as by being "benign," "malicious," and so forth.

For purposes of explanation, however, examples are provided in which a target organism is a malicious organism and a target signature is a malicious-genetic-sequence snippet. These examples are provided for purposes of explanation and are not intended to be limiting. The detection of such a signature in a sequence to be analyzed can indicate, with some level of certainty, that the sequence contains malicious genetic code. For example, if the sequence is a sequence that has been requested for synthesis, synthesis of the sequence can be rejected or postponed until further investigation and review is completed. It is to be appreciated that, although in some examples the principles of the disclosure may be applicable to synthesis procedures (for example, to aid in a determination as to whether or not to perform a synthesis procedure), the principles of the disclosure are not limited to examples involving synthesis. Accordingly, no limitation is implied by examples involving synthesis, which are provided solely for purposes of explanation.

Such signatures can also be used to categorize sequences according to the types of organisms (malicious or not) for which the sequence contains genetic information. In other examples, samples may be analyzed to determine whether a sequence contains target genetic code to identify target organisms in the sample. For example, a sample may be analyzed to determine whether the sample includes the SARS-CoV-2 coronavirus.

To identify signatures of malicious organisms, a sequence of a known malicious organism and sequences for one or more known benign organisms may be used. The respective sequences are broken into relatively short snippets, and malicious organism snippets compared to benign organism snippets. For more efficient comparison, the benign organism snippets may be arranged in a probabilistic data structure, such as a Bloom filter. If a match is found—i.e., the malicious organism snippet is also present in benign organisms—then the malicious organism snippet is not a suitable signature for the malicious organism. On the other hand, if the malicious organism signature snippet is only known to be present in the malicious organism, the malicious organism snippet may be a suitable signature. Suitable signatures may be stored in a malicious signature database along with metadata about the snippet or the corresponding malicious organism, including the organism's species, an identifier of a sample from which the snippet was taken, and/or the location of the snippet within that sample.

In some examples, a set of signatures may be filtered to identify a smaller set of one or more universal signatures. For example, a group of variants of a known malicious organism-such as sequences of several variants of the severe acute respiratory syndrome coronavirus 2 (SARS-CoV-2) virus, which causes coronavirus disease 2019 (COVID-19)—may be analyzed to obtain one or more target signatures. As discussed above, each of the target signatures may be identified as a signature because it is not present in any of the sequences of the one or more known benign organisms, and thus may uniquely identify malicious organisms.

The group of target signatures may subsequently be filtered by identifying those of the target signatures that are present in every variant of the group of variants. The target signatures in this subset may be referred to as "universal signatures" inasmuch as each signature is universally present in all the variants of the malicious organism. For example, consider a group of variants of the SARS-CoV-2 virus. A universal signature is a signature that is present in a sequence of each of the variants of the SARS-CoV-2 virus, and that is not present in one or more sequences of benign organisms used to generate the universal signature. The universal signatures may optionally be further processed and stored in a signature database for subsequent analysis.

In one approach, an unknown sequence (e.g., one provided by a customer) can be tested by comparing it to a signature database that can quickly determine whether the sequence contains one or more signature snippets, thereby identifying the sequence as potentially malicious. Metadata stored with the snippet may be used to facilitate or refine the identification, determine a level of confidence in the identification, or may be provided to other systems or users for further analysis. In a second approach, a sequence to be tested can be compared to multiple such filters, each of which contains signatures for a particular category of organism. For example, one filter may identify influenza signature snippets, and another filter may identify anthrax signature snippets. For more efficient categorization, each filter of signature snippets may be arranged in a probabilistic data structure, such as a Bloom filter. In this manner, a sequence can be categorized according to one or more types of organisms for which it contains genetic information.

In some examples, an unknown sequence output by a sequencer (for example, a DNA sequence output by a DNA sequencer) based on a sample of one or more organisms may be analyzed before the sequencer has finished sequencing the sample. The analysis may be performed in real time or near-real time with the operation of the sequencer. That is, the analysis may be performed while the sequencer is still sequencing the sample. In some examples, the analysis may be performed at a rate that is approximately equal to, or greater than, the rate at which the sequencer sequences the sample, as measured in megabytes (MB) per minute. Accordingly, as used herein, "real time" or "near-real time" analysis refers to analysis that is performed on a test sequence as the test sequence is output by a sequencer, without any intentional delay not incidental to the analysis procedure being inserted between the test sequence being output by the sequencer and the test sequence being analyzed. In some examples, analysis may be considered "real time" or "near-real time" inasmuch as the analysis is performed at a rate that is approximately equal to, or greater than, the rate at which the sequencer sequences the sample, as measured in MB/minute. In some examples, analysis may be performed and/or completed on a particular portion of a genetic sequence within milliseconds of the genetic sequence being initially sequenced by a sequencer, before the sequencer has finished sequencing the sample. In other examples, analysis may be performed and/or completed on a particular portion of a genetic sequence within a different time, such as within nanoseconds, microseconds, seconds, and so forth.

A record may be kept of a number of times that a target is detected in the sequence. Because the entire sequence output by the sequencer may be analyzed in some examples, there may be many opportunities to identify a malicious snippet indicating that the target is represented by the sequence. A probability that each of one or more threats is present in the sample may be determined based on the number of times that each threat was identified. For example, a low probability may be assigned to a threat that is only identified one time in the sequence, whereas a high probability may be assigned to a threat that is identified more than 100 times in the sequence.

The systems and methods described herein are not limited to the identification and/or classification of malicious organisms. For example, in some application, genetic sequences (e.g., from non-malicious organisms) may be compared against a signature database to identify species, taxa, or other category of organism.

According to one aspect, a method of identifying regions of malicious organic sequences is provided. The method includes identifying a plurality of benign snippets derived from a first sequence obtained from at least one benign organism; extracting a plurality of candidate signature snippets from a second sequence obtained from a malicious organism; determining, for each of the plurality of candidate signature snippets, whether the candidate signature snippet matches at least one of the plurality of benign snippets; and responsive to the candidate signature snippet not matching the at least one of the plurality of benign snippets, identifying the candidate signature snippet as a malicious signature snippet.

In one embodiment, the method includes determining if the malicious signature snippet is present in at least one test sequence. In a further embodiment, the method includes determining, for a plurality of malicious signature snippets present in the least one test sequence, a common characteristic of the plurality of malicious signature snippets. In yet a further embodiment, determining the common characteristic of the plurality of malicious signature snippets is performed with reference to metadata about at least one snippet of the plurality of malicious signature snippets. In a further embodiment, the metadata includes at least one of an identifier of a genus of an organism from which the snippet was obtained, an identifier of a species of an organism from which the snippet was obtained, and a location at which the snippet was generated on the second sequence.

In another embodiment, the plurality of benign snippets and the candidate signature snippet are one of DNA snippets, RNA snippets, and amino acid snippets. In another embodiment, the plurality of benign snippets is arranged in a probabilistic data structure. In a further embodiment, the probabilistic data structure is one of a Bloom filter and a search tree. In one embodiment identifying the plurality of benign snippets comprises extracting the plurality of benign snippets from the first sequence obtained from at least one benign organism. In another embodiment, the at least one benign organism is a non-malicious strain of an organism having at least one malicious strain. In yet another embodiment, the at least one benign organism belongs to a genus having at least one malicious organism.

In another embodiment, the method includes predicting a minimum number of benign snippets to be included in the plurality of benign snippets, the minimum number sufficient to yield a false positive rate below a threshold, the false positive rate being a rate at which candidate signature snippets identified as malicious signature snippets are present in a sequence of a benign organism. In a further embodiment, the minimum number of benign snippets is selected with reference to a malicious organism type.

In one embodiment, the plurality of benign snippets is a plurality of n-length subsequences of the first sequence, and the malicious snippet is an n-length subsequence not in the plurality of n-length subsequences.

In another embodiment, the plurality of candidate signature snippets includes a first plurality of n-length subsequences of the sequence, the first plurality of n-length subsequences each beginning at different positions of the sequence, and the plurality of benign snippets includes a second plurality of n-length subsequences of a known benign sequence, the second plurality of n-length subsequences each beginning at different positions of the known benign sequence. In another embodiment, the malicious snippet is a genetic sequence of a pathogen. According to another aspect, a system is provided. The system includes a benign snippet database configured to store a plurality of benign snippets from a first sequence obtained from at least one benign organism, and a processor configured to extract a plurality of candidate signature snippets from a second sequence obtained from a malicious organism; determine, for each of the plurality of candidate signature snippets, whether the candidate signature snippet matches at least one of the plurality of benign snippets; and responsive to the candidate signature snippet not matching the at least one of the plurality of benign snippets, identify the candidate signature snippet as a malicious signature snippet.

According to another aspect, a method of classifying biological sequences is provided. The method includes generating a first plurality of sequence snippets from a first plurality of organisms having a first trait; generating a second plurality of sequence snippets from a second plurality of organisms having a second trait; identifying a plurality of benign sequence snippets; and filtering the first plurality of sequence snippets and the second plurality of sequence snippets to remove at least one of the plurality of benign sequence snippets.

According to one embodiment, the method includes determining if a test sequence is present in the first plurality of sequence snippets; responsive to the test sequence being present in the first plurality of sequence snippets, identifying the test sequence as having the first trait; determining if the test sequence is present in the second plurality of sequence snippets; and responsive to the test sequence being present in the second plurality of sequence snippets, identifying the test sequence as having the second trait.

According to another embodiment, the first plurality of sequence snippets, the second plurality of sequence snippets, and the plurality of benign sequence snippets are one of DNA snippets, RNA snippets, and amino acid snippets.

According to yet another embodiment, the first plurality of sequence snippets is arranged in a first probabilistic data structure, and the second plurality of sequence snippets is arranged in a second probabilistic data structure. According to a further embodiment, the first probabilistic data structure and the second probabilistic data structure are each one of a Bloom filter and a search tree.

According to another embodiment, the first trait identifies a first class of pathogens and the second trait identifies a second class of pathogens.

According to at least one example, a method of analyzing an output of a sequencer in real time is provided, the method comprising identifying a group of genetic targets, obtaining a plurality of target signature snippets responsive to identifying the group of genetic targets, each target signature snippet being derived from a genetic sequence of a respective genetic target of the group of genetic targets, receiving a plurality of portions of a test sequence output by a sequencer sequencing a sample in real time, determining, in real time or near-real time with the sequencer sequencing the sample, whether at least one target signature snippet of the plurality of target signature snippets is present in at least one portion of the test sequence of the plurality of portions of the test sequence, determining, for each genetic target of the group of genetic targets, a respective probability the respective genetic target is present in the sample based at least on the determination of whether at least one target signature snippet of the plurality of target signature snippets is present in the at least one portion of the test sequence of the plurality of portions of the test sequence, and outputting an analysis of the sample, the analysis indicating the respective probability that each genetic target is present in the sample.

In various examples, the plurality of portions of the test sequence includes a first portion and a second portion, and wherein the first portion of the test sequence output by the sequencer is received before the second portion of the test sequence is generated by the sequencer. In at least one example, the method includes filtering the plurality of portions of the test sequence prior to determining whether at least one target signature snippet of the plurality of target signature snippets is present in at least one portion of the test sequence of the plurality of portions of the test sequence. In various examples, filtering the plurality of portions of the test sequence includes removing low-quality portions of the test sequence from the plurality of portions of the test sequence. In at least one example, low-quality portions of the test sequence include portions of the test sequence having greater than a threshold number of nucleobases repeated in a row.

In various examples, the method includes determining, for each genetic target of the group of genetic targets, a count value indicative of a number of times that at least one respective target signature snippet of a respective plurality of target signature snippets corresponding to the respective genetic target was determined to be present in the test sequence. In at least one example, determining, for each genetic target of the group of genetic targets, a respective probability the respective genetic target is present in the sample is based on a respective count value of the respective genetic target. In various examples, a respective probability the respective genetic target is present in the sample increases as the respective count value of the respective genetic target increases. In at least one example, the method includes determining whether a respective count value of each respective genetic target exceeds a respective threshold number, and determining that a respective genetic target is present in the sample based on the respective count value exceeding the threshold number.

According to at least one example, a system for analyzing an output of a sequencer in real time is provided, the system comprising a memory, at least one database configured to store target signature snippets, at least one processor coupled to the memory and to the at least one database and configured to identify a group of genetic targets, obtain, from the at least one database, a plurality of target signature snippets responsive to identifying the group of genetic targets, each target signature snippet being derived from a genetic sequence of a respective genetic target of the group of genetic targets, receive a plurality of portions of a test sequence output by a sequencer sequencing a sample in real time, determine, in real time or near-real time with the sequencer sequencing the sample, whether at least one target signature snippet of the plurality of target signature snippets is present in at least one portion of the test sequence of the plurality of portions of the test sequence, determine, for each genetic target of the group of genetic targets, a respective probability the respective genetic target is present in the sample based at least on the determination of whether at least one target signature snippet of the plurality of target signature snippets is present in the at least one portion of the test sequence of the plurality of portions of the test sequence, and output an analysis of the sample, the analysis indicating the respective probability that each genetic target is present in the sample.

In various examples, the plurality of portions of the test sequence includes a first portion and a second portion, and wherein the first portion of the test sequence output by the sequencer is received before the second portion of the test sequence is generated by the sequencer. In at least one example, the system further comprises the sequencer. In various examples, the at least one processor is further configured to filter the plurality of portions of the test sequence prior to determining whether at least one target signature snippet of the plurality of target signature snippets is present in at least one portion of the test sequence of the plurality of portions of the test sequence. In at least one example, filtering the plurality of portions of the test sequence includes removing low-quality portions of the test sequence from the plurality of portions of the test sequence. In various examples, low-quality portions of the test sequence include portions of the test sequence having greater than a threshold number of nucleobases repeated in a row.

In at least one example, the at least one processor is further configured to determine, for each genetic target of the group of genetic targets, a count value indicative of a number of times that at least one respective target signature snippet of a respective plurality of target signature snippets corresponding to the respective genetic target was determined to be present in the test sequence. In various examples, determining, for each genetic target of the group of genetic targets, a respective probability the respective genetic target is present in the sample is based on a respective count value of the respective genetic target. In at least one example, a respective probability the respective genetic target is present in the sample increases as the respective count value of the respective genetic target increases. In various examples, the at least one processor is further configured to determine whether a respective count value of each respective genetic target exceeds a respective threshold number, and determine that a respective genetic target is present in the sample based on the respective count value exceeding the threshold number.

According to various examples, a non-transitory computer-readable medium storing thereon sequences of computer-executable instructions for analyzing an output of a sequencer in real time is provided, the sequences of computer-executable instructions including instructions that instruct at least one processor to identify a group of genetic targets, obtain a plurality of target signature snippets responsive to identifying the group of genetic targets, each target signature snippet being derived from a genetic sequence of a respective genetic target of the group of genetic targets, receive a plurality of portions of a test sequence output by a sequencer sequencing a sample in real time, determine, in real time or near-real time with the sequencer sequencing the sample, whether at least one target signature snippet of the plurality of target signature snippets is present in at least one portion of the test sequence of the plurality of portions of the test sequence, determine, for each genetic target of the group of genetic targets, a respective probability the respective genetic target is present in the sample based at least on the determination of whether at least one target signature snippet of the plurality of target signature snippets is present in the at least one portion of the test sequence of the plurality of portions of the test sequence, and output an analysis of the sample, the analysis indicating the respective probability that each genetic target is present in the sample.

Still other aspects, embodiments, and advantages of these exemplary aspects and embodiments are discussed in detail below. Embodiments disclosed herein may be combined with other embodiments in any manner consistent with at least one of the principles disclosed herein, and references to "an embodiment," "some embodiments," "an alternate embodiment," "various embodiments," "one embodiment," or the like are not necessarily mutually exclusive and are intended to indicate that a particular feature, structure, or characteristic described may be included in at least one embodiment. The appearances of such terms herein are not necessarily all referring to the same embodiment.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures.

DETAILED DESCRIPTION

Figure 1:
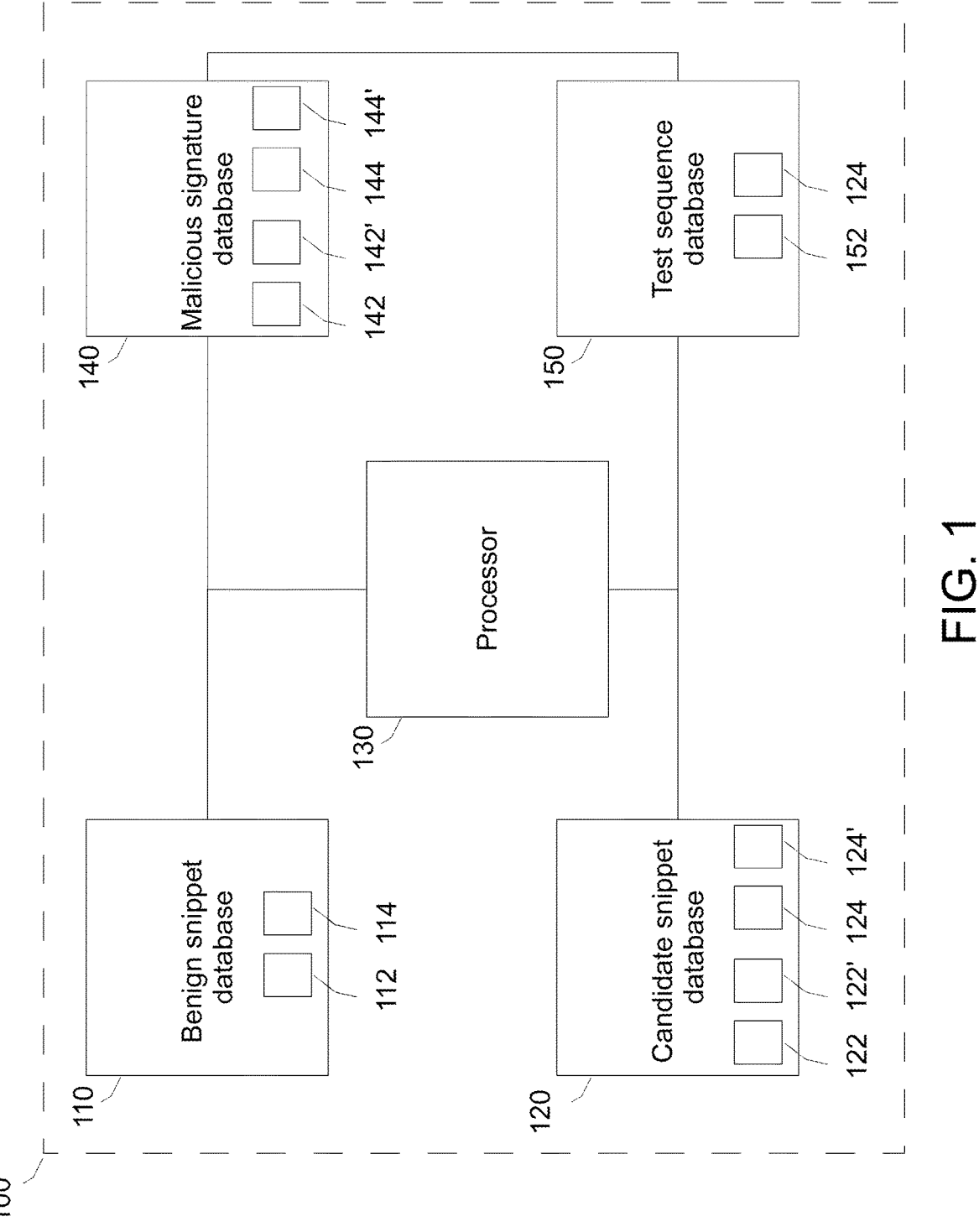
FIG. 1 is a block diagram of a computer system for identifying signature snippets and comparing them to test sequences according to aspects of the disclosure.

Systems and methods of identifying and classifying genetic sequences are described. For example, genetic signatures of malicious organisms (e.g., pathogens like anthrax or influenza) may be isolated. Such malicious organism signatures may be snippets of genetic sequences that are present in a malicious organism, but not present in related benign organisms, thereby uniquely identifying the sequence of the malicious organism. Once such malicious organism signatures have been identified, test sequences of unknown makeup can be compared to the malicious organism signatures to quickly determine if the test sequence contains the malicious organism signature. If so, the test sequence may be flagged for further investigation and/or may be identified as containing malicious sequence information.

Different approaches may be used for identifying and/or classifying malicious sequences. According to one approach, a benign snippet database is populated with sequences from known benign organisms. The sequences may represent deoxyribonucleic acid (DNA) sequences, ribonucleic acid (RNA) sequences, other nucleic acid sequences, amino acid sequences, or the like. The benign snippet database may be arranged as a probabilistic data structure, such as a Bloom filter, and the benign organisms may be selected for their similar structure or classification with malicious organisms of interest.

The system is "trained" by identifying one or more signature snippets for a particular malicious organism. In the training process, a sequence from the malicious organism is broken into candidate signature snippets. The benign snippet database is then examined to determine if each candidate signature snippet is present. If the candidate signature snippet is present in the benign snippet database, the candidate signature snippet is not a suitable signature snippet, i.e., it is not useful in identifying malicious organisms, since it is present in malicious and benign organisms alike. On the other hand, if the candidate signature snippet is not present in the benign snippet database, the candidate snippet may be a malicious signature snippet of use in identifying malicious organisms. That is, the presence of the malicious signature snippet in a test sequence would mean that the test sequence did not originate from any of the benign organisms represented in the benign snippet database. Malicious signature snippets can then be organized in a malicious signature database as part of the training process. Metadata about the snippet and/or the corresponding malicious organism may also be stored, including the organism's species, an identifier of a sample from which the snippet was taken, and the location of the snippet within that sample.

After the training process is complete, the system may test sequences of unknown makeup to determine if they contain any of the malicious signature snippets identified in the training process. A match between a test sequence snippet and a malicious signature snippet in the malicious signature database indicates that the test sequence may contain sequence information for a malicious organism, and the test sequence may be flagged for further review. Metadata stored about a malicious signature snippet matching a region of the test sequence snippet may be referenced to identify or categorize the test sequence or the test sequence snippet. For example, where multiple malicious signature snippets are found in the test sequence, common characteristics of the matching malicious signature snippets may be determined from the metadata. It may be determined, for example, that the matching malicious signature snippets are all from a particular sample (or related samples) of a specific organism, which may suggest that the customer is trying to replicate that organism.

According to another approach, a plurality of signature databases may be employed, with each signature database housing signature snippets for a particular known type or class of organism. For example, an influenza signature database may store signature snippets uniquely present in one or more sequences of influenza organisms, and likewise with an anthrax signature database. In the training process, the snippets in each signature database may be compared to one or more benign snippet databases, as in the approach above, to filter out any snippets present in the benign snippet database, leaving only signature snippets for the organisms represented by the particular signature database.

Test sequences of unknown makeup can then be broken into test sequence snippets and compared to each of the plurality of signature databases. The presence of a test sequence snippet in a particular signature database may indicate that the test sequence snippet contains information for the corresponding organism type. For example, a match of a test sequence snippet with a signature snippet in the influenza signature database may indicate that the test sequence contains some or all of the sequence for an influenza pathogen. Different test sequence snippets from a particular test sequence may match signature snippets in multiple signature databases. The number of matches and/or the location of matches in the test sequence may be used to classify the test sequence, or regions thereof, according to one or more organism types for which it may contain sequence information.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

FIG. 1 is a block diagram for a system 100 configured to perform methods of identifying target signature snippets, which may be malicious signature snippets. What is considered a "target organism," and what distinguishes a target organism from a "non-target organism," may be controlled or selected by a user. For clarity of explanation, FIG. 1 provides an example in which a target organism may be a malicious organism, and a non-target organism may be a benign organism, but it is to be appreciated that this example is non-limiting.

The system 100 includes a benign snippet database 110 configured to store a number of benign snippets 112, 114 derived from benign organism sequences (not shown). In some examples, the benign snippet database 110 may be considered a "non-target-snippet database" inasmuch as it stores snippets derived from non-target-organism sequences. The system 100 further includes a candidate signature database 120 configured to store a number of candidate signature snippets 122, 124 derived from malicious organism sequences (not shown), or "target-organism sequences," as well as metadata 122', 124' relating to the candidate signature snippets 122, 124. For example, the metadata 122', 124' may indicate taxonomic information indicative of a biological classification of the organism from which the candidate signature snippets 122, 124 are derived. It is to be appreciated that the system 100 is described as containing several different databases 110, 120, 140, 150 for purposes of explanation. In some examples, the system 100 may include additional or fewer databases (including a single database) configured to store the information stored by the databases 110, 120, 140, 150.

The system 100 also includes a processor 130 configured to compare each of the candidate signature snippets 122, 124 to the benign snippet database 110 to determine if a given candidate signature snippet 122, 124 matches any of the benign snippets 112, 114. In at least one example, a given candidate signature snippet 122, 124 "matches" any of the benign snippets 112, 114 if the given candidate signature snippet 122, 124 is an exact match of any of the benign snippets 112, 114. If candidate signature snippet 122 matches benign snippet 112, it is known that the candidate signature snippet 122 does not uniquely identify the malicious organism sequence. On the other hand, if candidate signature snippet 124 does not match either of benign snippets 112, 114, the candidate signature snippet 124 may uniquely identify the malicious organism sequence. In that case, the candidate signature snippet 124 may be stored in a malicious signature database 140 as one of the malicious signature snippets 142, 144. In some examples, the malicious-signature database 140 may be considered a "target-snippet database" inasmuch as it stores snippets derived from target-organism sequences. The malicious signature database 140 may further store metadata 142', 144' relating to the malicious signature snippets 142, 144. For example, the metadata 142', 144' may indicate taxonomic information indicative of a biological classification of the organism from which the malicious signature snippers 142, 144 are derived.

The system 100 further includes a test sequence database 150 configured to store a number of test sequences 152, 154. During a testing operation of the system 100, one or more of the test sequences 152, 154 in the test sequence database 150 is compared to the malicious signature snippets 142, 144 to determine if the malicious signature snippets 142, 144 are present in the one or more of the test sequences 152, 154. If so, any of the test sequences 152, 154 matching any of the malicious signature snippets 142, 144 may be flagged as containing a sequence (or signature snippet thereof) of a malicious organism (or, more generally, a target organism). In some embodiments, the one or more test sequences 152, 154 may be full genetic sequences (e.g., representing full strands of DNA, other nucleic acid sequences, amino acid sequences, and so forth). In other embodiments, the one or more test sequences 152, 154 may be sub-sequences of a given length, with an optimal length for testing being selected. In preferred embodiments, the entire one or more test sequence 152, 154 is analyzed, such as in sequential order. In some embodiments, the one or more test sequences 152, 154 may first be compared to the malicious signature snippets 142, 144 at locations on the one or more test sequences 152, 154 where malicious signatures may be expected to be found. If no matches are found, less likely locations may be examined.

In some embodiments, a user interface may be used to display or otherwise provide results of the comparison, and/or to issue an alert or other communication that the test sequence may represent a malicious organism.

The benign snippet database 110 may be structured as a space-efficient probabilistic data structure, such as a Bloom filter. Such filters can be used to quickly and efficiently test whether an element is a member of a set. In the present context, such a filter can be used to quickly determine whether a candidate signature snippet matches (for example, exactly matches) one or more benign snippet in the benign snippet database 110 (in which case the candidate signature snippet is definitively not suitable as a malicious signature snippet), or, alternately, whether the candidate signature snippet does not match (for example, does not exactly match) any benign snippet in the benign snippet database 110 (in which case the candidate signature snippet may be suitable as a malicious signature snippet).

A "false positive" can occur where a candidate signature snippet does not match any benign snippet in the benign snippet database 110, but nonetheless is not unique to a malicious organism sequence—for example, the candidate signature snippet may match a benign snippet that would have been generated from a benign organism sequence on which extraction was not performed. In this situation, a false-positive identification of a malicious signature snippet could cause benign organism sequences to be mistakenly identified as malicious organism sequences during the testing phase of operation, thereby requiring additional (and unnecessary) investigation. To reduce the occurrence of false positives to an acceptable level, a sufficiently large number of benign snippets may be populated in the benign snippet database 110; as the size of the benign snippet database 110 grows, the rate of false-positives approaches zero. In one example for a given organism type, generating benign snippets from a collection of 1.5 million base pairs of benign sequences may yield a false-positive rate of 4%. Increasing the population of base pairs by a factor of ten (to 11.5 million) may reduce the false-positive rate to 0.25%.

In some embodiments, the benign snippet database 110 may be prepopulated with the benign snippets 112, 114 (e.g., from an external source) such that extraction by the system 100 of the benign snippets 112, 114 from benign organism sequences is not necessary. In other embodiments, the benign snippet database 110 and/or the processor 130 may be configured to extract the benign snippets 112, 114 from sequences obtained from one or more known benign organisms. The length n of snippets may be configurable, and snippets of a given length n are referred to herein as n-grams. While the examples shown here use 3-gram snippets, any feasible length n may be used.

Figure 2A:
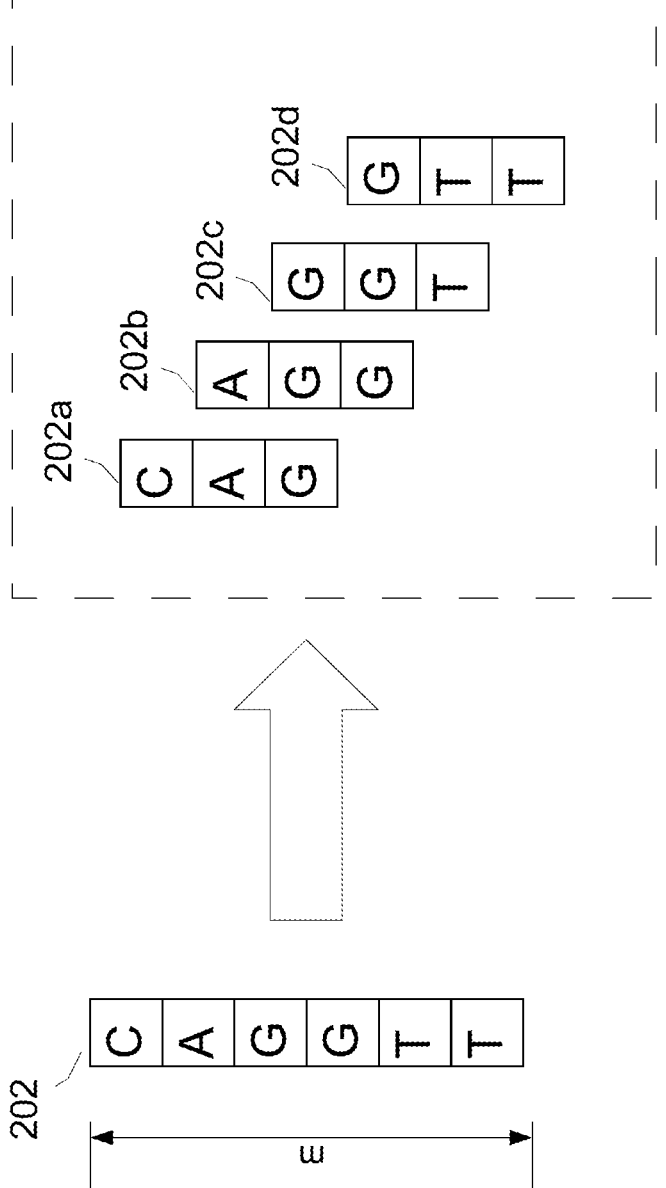
FIG. 2A illustrates the extraction of benign snippets according to aspects of the disclosure.

FIG. 2A shows how an exemplary benign DNA sequence 202 ("CAGGTT") from a benign organism and including six nucleotides can be extracted into multiple 3-gram snippets 202a-d for storage in the benign snippet database 110 according to some embodiments. It is to be appreciated that DNA is provided as an example for purposes of illustration only, and that the principles of the disclosure are also applicable to other nucleic acids, such as RNA, amino acid sequences, and so forth. Each of the 3-gram snippets 202a-d represents a subsequence of the nucleotides of benign DNA sequence 202 at a different starting point. For example, the first 3-gram snippet 202a contains the 3-nucleotide subsequence ("CAG") starting at the first position of the benign DNA sequence 202, the second 3-gram snippet 202b contains the 3-nucleotide subsequence ("AGG") starting at the second position of the sequence 202, and so forth. A DNA sequence of length m may therefore yield m−n snippets.

Returning to FIG. 1, the candidate signature database 120 and/or the processor 130 may be configured to derive the candidate signature snippets 122, 124 from sequences obtained from one or more known malicious organisms to be detected during the testing phase of operation of the system 100. The length of the candidate signature snippets 122, 124 may be selected to be the same as the n-gram benign snippets (e.g., 3).

Figure 2B:
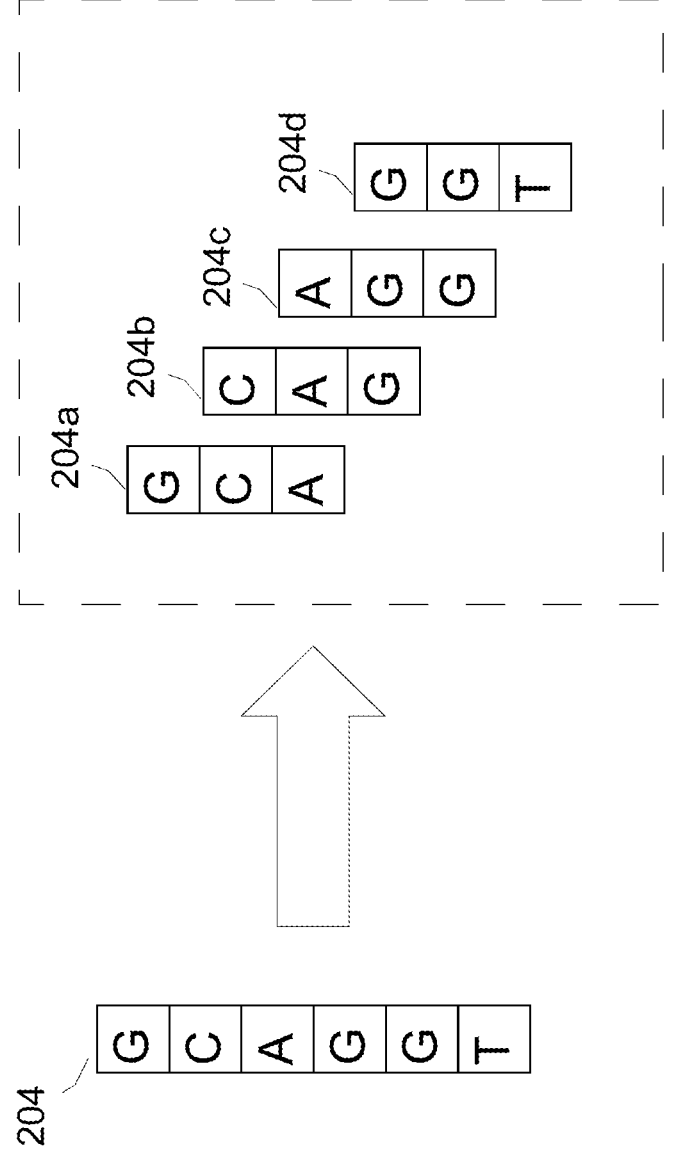
FIG. 2B illustrates the extraction of candidate signature snippets according to aspects of the disclosure.

FIG. 2B shows how a malicious DNA sequence 204 can be extracted into multiple 3-gram snippets 204a-d for storage in the candidate signature database 120 according to some embodiments. The extraction is performed in much the same way as with the benign DNA sequence 202 in FIG. 2A. For example, the first 3-gram snippet 204a contains the 3-nucleotide subsequence ("GCA") starting at the first position of the malicious DNA sequence 202, the second 3-gram snippet 204b contains the 3-nucleotide subsequence ("CAG") starting at the second position of the sequence 204, and so forth.

The processor 130 is further configured to identify those candidate signature snippets 122, 124 in the candidate signature database 120 that do not match any of the benign snippets 112, 114 in the benign snippet database 110. Candidate signature snippets 122, 124 without such a match can be identified as malicious signature snippets 142, 144 and stored in the malicious signature database 140. Referring to FIGS. 2A and 2B, for example, candidate signature snippet 204b ("CAG") matches benign snippet 202a, candidate signature snippet 204c ("AGG") matches benign snippet 202b, and candidate signature snippet 204d ("GGT") matches benign snippet 202c. Thus, none of candidate signature snippets 204b, 204c, or 204d would be identified as malicious signature snippets. Candidate signature snippet 204a ("GCA") has no match in the benign snippet database 110, however, and would be identified as a malicious signature snippet.

Returning to FIG. 1, any malicious signature snippets 142, 144 identified by the processor 130 are stored in the malicious signature database 140.

Each of the benign snippet database 110, the candidate signature database 120, and/or the malicious signature database 140 may be arranged, populated, or optimized to improve performance. For example, duplicate snippets in a given database may be removed, and the snippets stored therein may be sorted or filtered for optimization purposes.

As discussed in greater detail below, for example, target snippets may be filtered to identify a subset of universal target signatures. In some embodiments, the benign snippet database 110, the candidate signature database 120, and/or the malicious signature database 140 may be stored in an encrypted format, or otherwise secured against access by unauthorized parties, and decrypted at or shortly before runtime.

The candidate signature database 120 and/or the malicious signature database 140 may also store metadata 122', 124', 142', 144' about the snippets they respectively store, or about the corresponding malicious organism. Such metadata may include, for example, a data/time at which the snippet was created; an identifier of the sample/organism from which the snippet was obtained; the location of the snippet in that sample; a unique identifier of the snippet; a species or genus of the corresponding organism; a general category of the organism (e.g., virus, bacteria); or the like.

Figure 3:
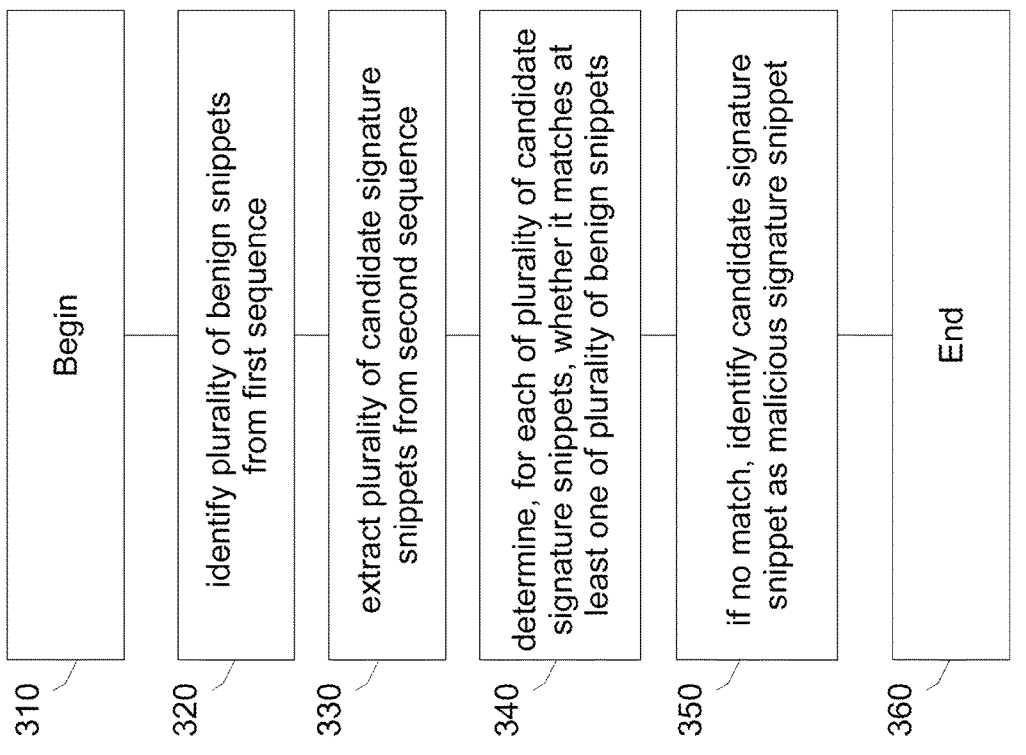
FIG. 3 is a flow diagram of one example of a process of identifying signature snippets according to aspects of the disclosure.

FIG. 3 is a flow diagram for one example of a method 300 for identifying regions of malicious genetic sequences.

Method 300 begins at step 310.

At step 320, a plurality of benign snippets is identified, the plurality of benign snippets derived from a first sequence obtained from at least one benign organism. As is to be appreciated in light of the foregoing, step 320 may more broadly include identifying a plurality of non-target snippets derived from a first sequence obtained from at least one non-target organism. In some embodiments, the plurality of benign snippets is extracted from sequences from one or more known benign organisms, as discussed above with reference to FIG. 2A. In particular, benign snippets of length n may be extracted from such benign sequences. The length n of such snippets may be selected to be sufficient to facilitate the identification of malicious signature snippets in later steps. For example, consider a scenario in which a snippet of length n=20 is necessary to uniquely identify a malicious sequence—in other words, there would be no snippets of length n<20 that would be present in a malicious sequence but not present in a benign sequence. In such a scenario, the length n of both the benign snippets and the malicious signature snippets may be 20 (or higher).

As discussed above with reference to FIG. 2A, benign snippets may be extracted from benign sequences by creating, where possible, an n-length snippet corresponding to a subsequence starting at each position in the benign sequence. In other words, each position (e.g., nucleotide) in the benign sequence, and the n subsequent positions (if available), may be represented by a benign snippet. In other embodiments, only certain positions in the benign sequence may be used as the basis for benign snippets. For example, the chemistry of the sequence or other parameters may make it impossible or unlikely for a malicious signature snippet to correspond to particular starting positions on the benign sequence, in which case those particular starting positions may not be used as the basis for extracting benign snippets.

In some embodiments, extraction of benign snippets from the one or more benign sequences may not be performed by the system. Rather, benign snippets may be provided to the system, for example, by a third party, with the extraction already performed. For example, a database of benign snippets may be made available. In another example, the benign snippets may have been extracted by the system during previous operations and maintained, and as such do not need to be extracted again. It will be appreciated that the extraction and/or use of benign snippets to train the system may be performed in a rolling manner, i.e., new benign snippets may be added over time to improve the accuracy of the results.

The plurality of benign snippets may be derived, in whole or in part, from at least one benign organism having at least one characteristic relevant or useful to identifying malicious signature snippets. In some embodiments, benign organisms that are similar in some manner to a malicious organism of interest may be used to extract benign snippets. The similarities between the benign organisms and the malicious organism may reflect similarities in their genetic sequences, allowing the system to identify the relative few differences as malicious signature snippets. For example, the benign organism may be a non-malicious strain of the malicious organism of interest. In another example, the benign organism and the malicious organism may belong to a common genus, or to a broader range of related organisms. In an example in which target organisms include SARS-CoV-2 and malicious variants thereof, benign organisms may include other coronaviruses, such as benign coronaviruses and/or coronaviruses that are not as malicious as SARS-CoV-2. In this example, a user may determine which organisms (for example, which coronaviruses) are to be considered benign, and it is these selected organisms from which the plurality of benign snippets are derived. As discussed in greater detail below, certain organisms may alternately be classified as "neutral," rather than as a target or non-target organism.

At step 330, a plurality of candidate signature snippets is extracted from a second sequence obtained from a malicious organism. As is to be appreciated in light of the foregoing, step 330 may more broadly include identifying a plurality of candidate signature snippets derived from a second sequence obtained from a target organism. Step 330 may be executed repeatedly such that a plurality of candidate signature snippets is extracted from a respective sequence obtained from each of a plurality of malicious (or target) organisms. In some embodiments, the extraction is performed as discussed above with reference to FIG. 2B. In particular, candidate signature snippets of length n may be extracted from sequences obtained from one or more malicious organisms. The length n of such snippets may be selected to be sufficient to facilitate the identification of malicious signature snippets in later steps.

At step 340, it is determined, for each of the plurality of candidate signature snippets, whether the candidate signature snippet matches at least one of the plurality of benign snippets. In at least one example, step 340 includes determining whether the candidate signature snippet exactly matches at least one of the plurality of benign snippets. In some embodiments, the plurality of benign snippets are arranged in the benign snippet database as a probabilistic data structure (e.g., a Bloom filter), and queries are made on the Bloom filter for each candidate signature snippet. In other embodiments, the plurality of benign snippets is organized in an array, a search tree, a relational database, a schema-free database, a collection of n-tuples, or otherwise stored and appropriately queried. In some embodiments, the plurality of benign snippets is de-duplicated, sorted, and/or filtered to increase efficiency.

At step 350, the candidate signature snippet is identified as a malicious signature snippet responsive to the candidate signature snippet not matching the at least one of the plurality of benign sequence snippets. In some embodiments, the candidate signature snippets identified as malicious signature snippets may be stored as malicious signature snippets in the malicious signature database, along with any metadata for the malicious signature snippets. In other embodiments, a separate malicious signature database may not be employed, and the candidate signature snippet may be flagged as a malicious signature snippet in the candidate signature database; at the end of the training process, those candidate signature snippets not flagged as malicious signature snippets may be discarded or otherwise not used during the testing process.

Process 300 ends at step 360.

In some examples, once the training process is complete, test sequences may be examined to determine if one or more malicious signature snippets are present; if so, the test sequence may be flagged for further review and/or considered for rejection from a synthesizing/replicating process in examples in which synthesis/replication is performed, for example, as discussed below with respect to FIG. 4. In various examples, once the process 300 is complete, malicious signature snippets (or "target signature snippets") are further processed. For example, target signature snippets may be filtered to identify one or more universal target signature snippets and/or one or more low-homology universal signature snippets, as discussed below with respect to FIG. 10. Furthermore, in some examples, test sequences may be examined to determine if one or more universal target signature snippets and/or one or more low-homology universal signature snippets are present in the test sequences; that is, in some examples, the malicious signature snippets provided in the process 300 may be filtered in accordance with FIG. 10 to identify universal target signature snippets, and the universal target signature snippets may be used to examine test sequences in accordance with FIG. 4.

Figure 4:
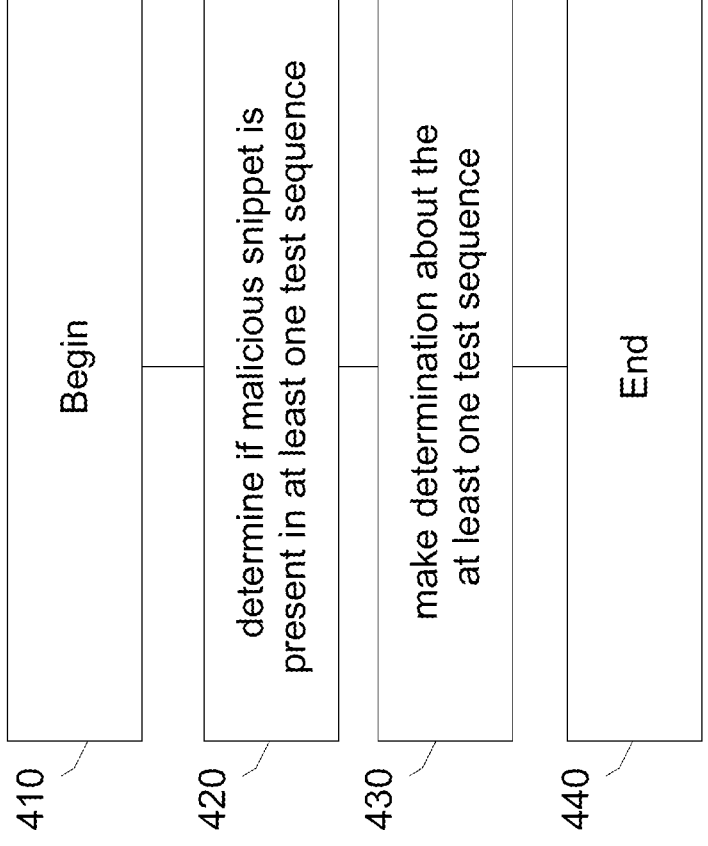
FIG. 4 is a flow diagram of one example of a process of testing test sequences according to aspects of the disclosure.

FIG. 4 is a flow diagram for one example of a method 400 for testing one or more test sequences for the existence of malicious signature snippets.

Method 400 begins at step 410.

At step 420, it is determined if the malicious signature snippet is present in at least one test sequence. In one example, the malicious signature snippet may include the candidate signature snippet identified as a malicious signature snippet at step 350, discussed above. In another example, the malicious signature snippet may include a universal target signature snippet identified at act 1008, discussed below. In another example, the malicious signature snippet may include a low-homology universal target signature snippet identified at act 1010, discussed below.

In some embodiments, the at least one test sequence is a sequence provided for purposes of replication. The sequence may represent a single genetic sequence, or may include regions intended to be "clipped and stitched" later using a mechanism such as CRISPR. In some embodiments, the at least one test sequence may be a full genetic sequence (e.g., representing a full strand of DNA). In other embodiments, the at least one test sequence may be a subsequences of the full genetic sequence. An optimal length of the subsequence, or portion of the full genetic sequence included in the subsequence, may be selected. For example, a test sequence may be a subsequence of a full genetic sequence, the subsequence selected from a location or region of the full genetic sequence based on a likelihood of finding a malicious signature snippet in that region. In still other embodiments, a subsequence may be selected to omit known benign regions of a full genetic sequence. In some examples, the at least one test sequence may be analyzed in real time or near-real time as the at least one test sequence is received, as discussed below with respect to FIG. 11. For example, at least one test sequence may be analyzed in real time as a sequencer produces the at least one test sequence.

Malicious signature snippets may be compared to the at least one test sequence at each sequential position on the at least one test sequence. For example, a 3-gram malicious signature snippet may first be compared to positions 1-3 on the at least one test sequence, then to positions 2-4 on the at least one test sequence, etc.

In some embodiments, the number and type of matches may be stored for each at least one test sequence and/or malicious signature snippet. For example, data may be stored indicating the location of each malicious signature snippet on the at least one test sequence, the type of the malicious signature snippet, a number of times each malicious signature snippet occurs in the at least one test sequence, and other information.

Metadata about the malicious signature snippets and/or the corresponding malicious organisms may be used to identify or categorize the test sequence. For example, where multiple malicious signature snippets are found in the test sequence, common characteristics of the matching malicious signature snippets may be determined from the metadata. It may be determined, for example, that the matching malicious signature snippets are all from a particular sample (or related samples) of a specific organism, which may suggest that the customer is trying to replicate that organism. Depending on the number of signature snippets in the test sequence, it may be possible to identify a genus, species, or even particular sample of malicious organism that is reflected in the test sequence.

The type and number of signature snippets corresponding to a malicious organism or organism type may be tracked and analyzed to draw conclusions about the test sequence. For example, if the number, cumulative length, or other statistic of influenza signature snippets in a test sequence exceeds a given threshold, a conclusion may be automatically made that the test sequence is an attempt to synthesize influenza. In another embodiment, such statistics may be used to determine a level of confidence in the determination that the sequence was submitted for nefarious purposes.

At optional step 430, a determination may be made about the at least one test sequence. For example, depending on the number and type of malicious signature snippets occurring on the at least one test sequence, and the malicious organisms to which they relate, a determination may be made to reject the at least one test sequence from a synthesizing/replicating application in non-limiting examples that include a synthesizing/replicating application, and/or to flag the at least one test sequence for further review by the system and/or a user. In some embodiments, a threshold number of occurrences of malicious signature snippets may be set, and a determination made about the at least one test sequence based on whether the threshold is exceeded. Different thresholds may be set for different malicious organisms, with more dangerous pathogens having a low/zero threshold, and less dangerous pathogens having a higher threshold.

Method 400 ends at step 440.

In addition to approaches described above for identifying the presence of malicious organism sequences, there are also applications where it would be useful to quickly categorize test sequences as one or more of a number of organisms (including, but not limited to, pathogens).

Figure 5:
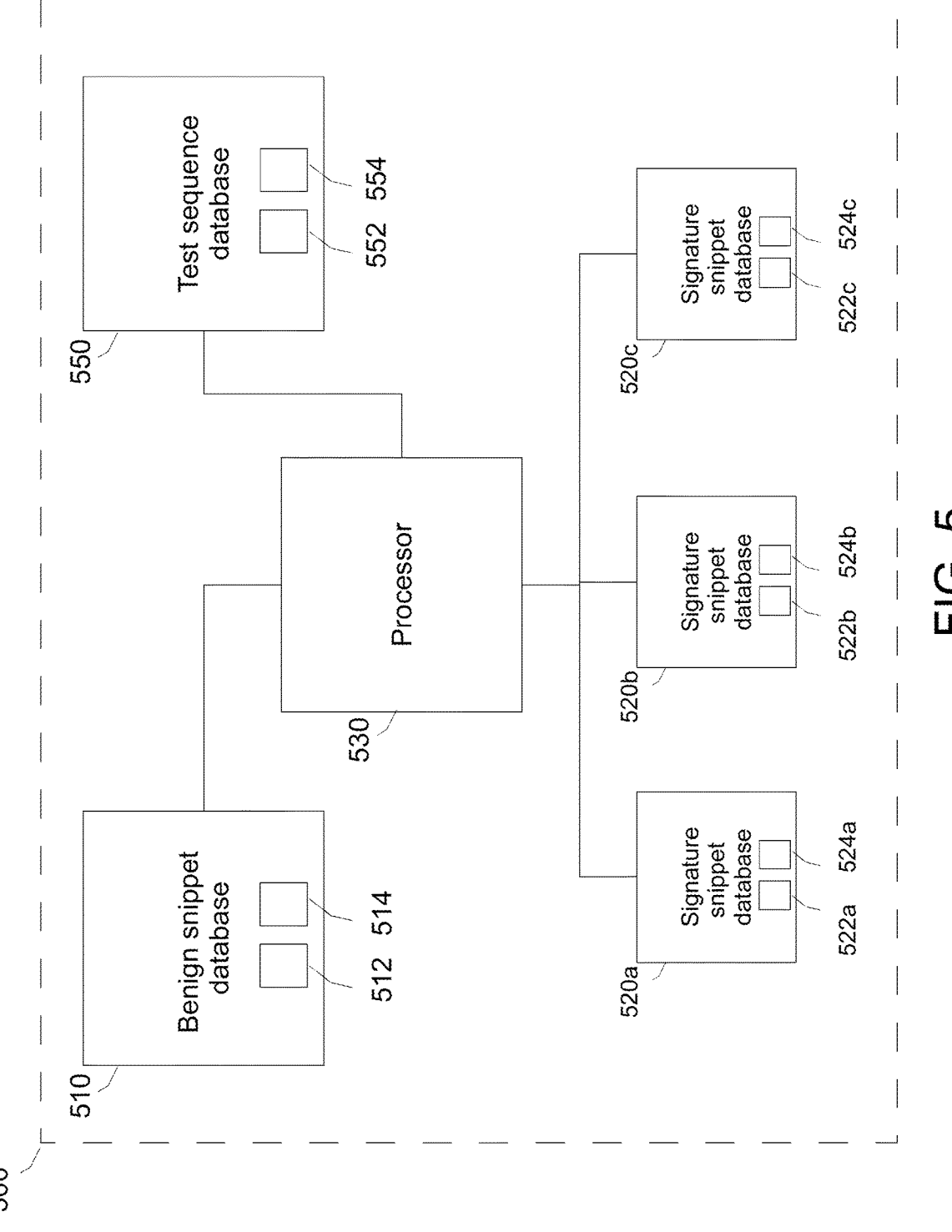
FIG. 5 is a block diagram of another computer system for identifying signature snippets and comparing them to test sequences according to aspects of the disclosure.

FIG. 5 is a block diagram for a system 500 configured to perform methods of identifying signature snippets that can be used to categorize unknown sequences. System 500 may be similar to system 100 in some aspects, with some differences discussed here.

The system 500 includes at least one benign snippet database 510 configured to store a number of benign snippets 512, 514 derived from benign organism sequences (not shown). The system 500 further includes a plurality of malicious signature databases 520a-c configured to store a number of candidate signature snippets 522a-c, 524a-c derived from malicious organism sequences (not shown). In this approach, each of the malicious signature databases 520a-c may also be organized as a probabilistic data structure, such as Bloom filter. Each of the malicious signature databases 520a-c may correspond to a different malicious organism type or group. For example, malicious signature database 520a may store signature snippets for influenza organisms; malicious signature database 520b may store signature snippets for anthrax organisms; and malicious signature database 520c may store signature snippets for the smallpox virus. Each malicious signature database may also store metadata (not shown) about the snippets stored therein, as described above with respect to malicious signature database 140.

The system 500 further includes a processor 530, configured to compare candidate signature snippets (not shown) to the plurality of benign snippet sequences 512, 514. If no match is found, it may be determined that a particular candidate signature snippet is a suitable signature snippet for a particular type of malicious organism associated with one of the malicious signature snippet databases 520a-c. If so, the candidate signature snippet may be stored in one of the malicious signature snippet databases (e.g., 520b) corresponding to the type of malicious organism. To continue the previous example, if a candidate signature snippet is found to be a suitable signature snippet for influenza, then the candidate signature snippet may be stored as a signature snippet 522a in malicious signature snippet database 520a.

As in system 100, candidate signature snippets in system 500 are extracted from a sequence of a known organism. While the examples discussed here involve malicious organisms, it will be appreciated that the same techniques may be used to identify or categorize non-malicious organisms of interest, as well. The candidate signature snippets may be stored in one or more candidate signature snippet databases (not shown).

Where candidate signature snippets are stored for a number of malicious organisms or malicious organism types, the candidate signature snippets may be stored in one or more databases in any number of manners that allows the candidate signature snippet to be associated with a particular organism or organism type. In one embodiment, candidate signature snippets may be stored in a single candidate signature snippet database, with each candidate signature snippet associated (by an identifier or other association) with a particular malicious organism or malicious organism type. In other embodiments, candidate signature snippets may be stored in different databases according to their associated malicious organism or organism type.

Benign snippets may similarly be stored in a common database, or may be stored separately according to the type of benign organism from which they originate, or according to the malicious organism or organism type for which they are used to identify signature snippets.

As in system 100, system 500 further includes a test sequence database 550 configured to store a number of test sequences 552, 554. During a testing operation of the system 500, one or more of the test sequences 552, 554 in the test sequence database 550 is compared to the signature snippets in one or more of malicious signature snippet databases 520a-c to determine if any of the malicious signature snippets 522*a-c*, 524*a-c* are present in the one or more of the test sequences 552, 554. For example, the test sequences 552, 554 may be applied to a Bloom filter of each of the malicious signature snippet databases 520-*ac* to determine if any matches are found. If so, any of the test sequences 552, 554 matching any of the malicious signature snippets 522*a-c*, 524*a-c* may be flagged as containing a sequence (or snippet thereof) of the malicious organism associated with the malicious signature snippet database 520*a-c* containing such malicious signature snippets.

In some embodiments, the one or more test sequences 552, 554 may be full genetic sequences (e.g., representing full strands of DNA). In other embodiments, the one or more test sequences 552, 554 may be subsequences of a given length, with an optimal length for testing being selected. In some embodiments, the one or more test sequences 552, 554 may first be compared to the malicious signature snippets 522*a-c*, 524*a-c* at locations on the one or more test sequences 552, 554 where malicious signatures may be expected to be found. If no matches are found, less likely locations may be examined.

Figure 6:
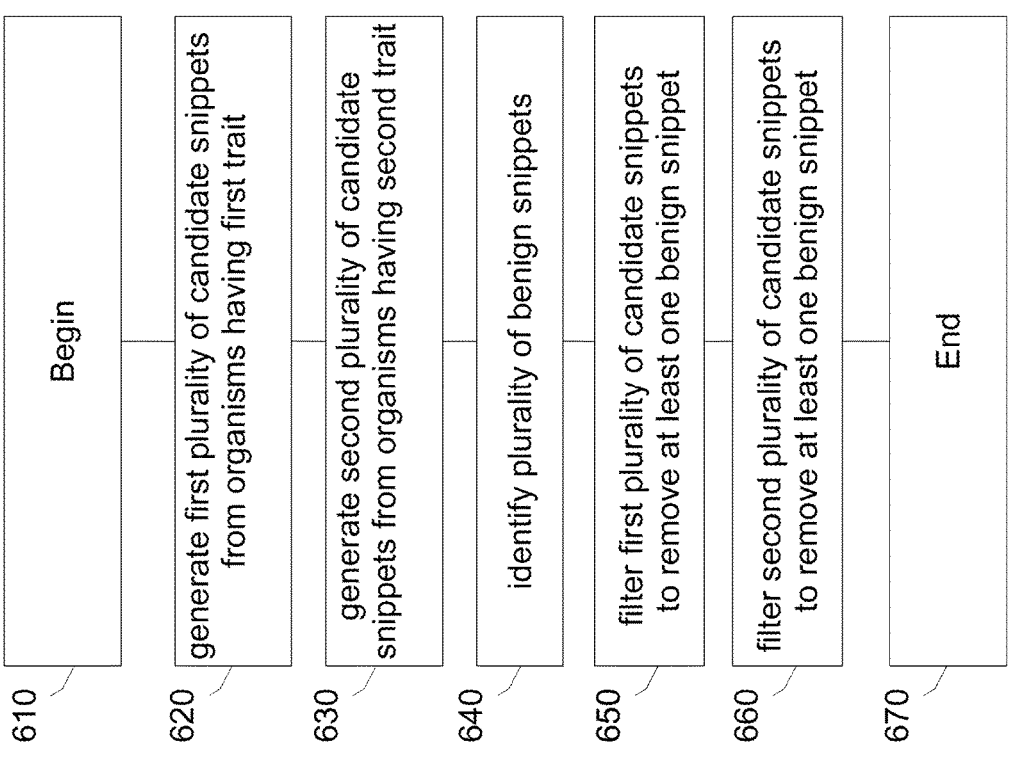
FIG. 6 is a flow diagram of one example of a process of identifying signature snippets according to aspects of the disclosure.

FIG. 6 is a flow diagram for one example of a method 600 for classifying regions of genetic sequences, such as with system 500.

Method 600 begins at step 610.

At step 620, a first plurality of sequence snippets is generated from a first plurality of organisms having a first trait, and at step 630 a second plurality of sequence snippets is generated from a second plurality of organisms having a second trait. In some embodiments, the extraction is performed as discussed above with reference to FIG. 2B. In particular, candidate signature snippets of length n may be extracted from sequences obtained from a plurality of malicious organisms having a first trait, and from a plurality of malicious organisms having a second trait. The trait may be a classification or category of the type of organism (e.g., influenza, coronavirus, and so forth).

In step 640, a plurality of benign sequence snippets is identified. Step 640 may be performed in much the same way as step 320 of method 300. As discussed above, in some embodiments, extraction of the plurality of benign sequence snippets may not be performed by the system. Rather, benign sequence snippets may be provided to the system, for example, by a third party, with the extraction already performed. For example, a database of benign snippets may be made available. In another example, the benign sequence snippets may have been extracted by the system during previous operations and maintained.

In step 650, the first plurality of candidate sequence snippets is filtered to remove at least one of the plurality of benign sequence snippets, and in step 660, the second plurality of candidate sequence snippets is filtered to remove at least one of the plurality of benign sequence snippets. Other pluralities of candidate sequence snippets may also be filtered, as the method is not limited to two such pluralities. Steps 650 and 660 may be performed in much the same way as step 340 of method 300. In particular, each plurality of candidate signature snippets is compared to the benign snippets (e.g., in a Bloom filter), and any candidate signature snippets matching a benign snippet may be identified as not being a suitable signature snippet. Those signature snippets found to be suitable may be stored in one of the malicious signature snippet databases corresponding to the type of organism uniquely identified by the signature snippet. The malicious signature snippet databases may be organized as a plurality of probabilistic data structures, such as a Bloom filter.

Method 600 ends at step 670.

In some examples, once the training process is complete, test sequences may be examined to determine if one or more malicious signature snippets are present; if so, the test sequence may be flagged for further review and/or considered for rejection from a synthesizing/replicating process in non-limiting examples that include a synthesizing/replicating process, for example, as discussed below with respect to FIG. 7. In various examples, once the method 600 is complete, malicious signature snippets (or "target signature snippets") are further processed. For example, target signature snippets may be filtered to identify one or more universal target signature snippets and/or one or more low-homology universal signature snippets, as discussed below with respect to FIG. 10. Furthermore, in some examples, test sequences may be examined to determine if one or more universal target signature snippets and/or one or more low-homology universal signature snippets are present in the test sequences; that is, in some examples, the malicious signature snippets provided in the method 600 may be filtered in accordance with FIG. 10 to determine universal target signature snippets, and the universal target signature snippets may be used to examine test sequences in accordance with FIG. 7.

Figure 7:
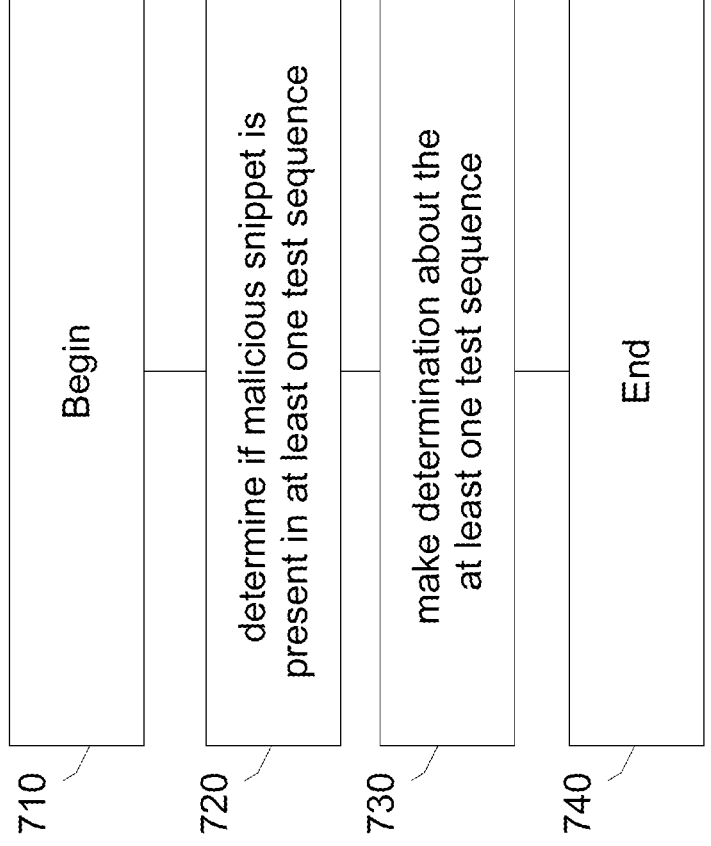
FIG. 7 is a flow diagram of one example of a process of testing test sequences according to aspects of the disclosure.

FIG. 7 is a flow diagram for one example of a method 700 for testing one or more test sequences for the existence of malicious signature snippets stored in one or more malicious signature databases.

Method 700 begins at step 710.

At step 720, it is determined if the malicious signature snippet is present in at least one test sequence. Step 720 may be performed similarly to step 420 of method 400. The at least one test sequence, or snippets thereof, may be compared to the one or more signature snippets stored (e.g., in Bloom filters) in a plurality of signature snippet databases. In some embodiments, the test sequence may be compared to all of the signature snippet databases, or some standard subset of the signature snippet databases. In other embodiments, particular signature snippet databases may be selected for comparison based on some known characteristic of the test sequence. For example, if it is determined that the test sequence is more likely to contain genetic sequences for a coronavirus, then the test sequence may not be compared to signature snippet databases unrelated to a coronavirus. In some embodiments, the signature snippet databases against which the test sequence is compared may be selectable by a user, e.g., an operator of system 500.

At optional step 730, a determination may be made about the at least one test sequence. Step 730 may be performed similarly to step 430 of method 400.

Method 700 ends at step 740.

As discussed above, the process 300 may be executed to identify, at act 350, a target signature snippet. Similarly, the process 600 may be executed to identify, at acts 650 and 660, target signature snippets. Each of the processes 300, 600, or specific acts thereof, may be executed several times to identify several target signature snippets. In some examples, several target signature snippets may be identified from a single organism (for example, a single SARS-CoV-2 virus). In other examples, several target signature snippets may be identified from each of several organisms (including, for example, several coronaviruses) in executing either or both of the processes 300, 600.

A group of organisms may include target organisms and non-target organisms. For example, consider a group of coronaviruses. Some coronaviruses may be considered non-targets at least because they are not harmful, or minimally harmful, to humans. Other coronaviruses, such as the SARS-CoV-2 coronavirus, may be considered targets at least because they are harmful to humans. Still other coronaviruses, such as the SARS-CoV-1 coronavirus, may be considered neutral at least because, while they may be harmful to humans, they have been largely eradicated from the world. Thus, such coronaviruses may be identified as neutral because they may be considered irrelevant inasmuch as such coronaviruses are extremely unlikely to be found in a sample.

It may be advantageous to be able to distinguish certain target coronaviruses from other non-target or neutral coronaviruses in a sample to determine whether a coronavirus in the sample is malicious or benign such that appropriate actions can be taken. Thus, it may be advantageous to define a first group of coronaviruses as target coronaviruses (for example, the SARS-CoV-2 virus and genetic variants thereof), a second group of coronaviruses as non-target coronaviruses, and a third optional group of coronaviruses as neutral coronaviruses. Furthermore, it may be advantageous to identify one or more universal target signature snippets that universally identify every coronavirus in the first group of coronaviruses, but do not identify any coronavirus in the second group of coronaviruses. Because the third group of coronaviruses is a neutral group, it may be irrelevant whether or not the universal target signature snippets do or do not identify any coronaviruses in the third group.

Figure 9:
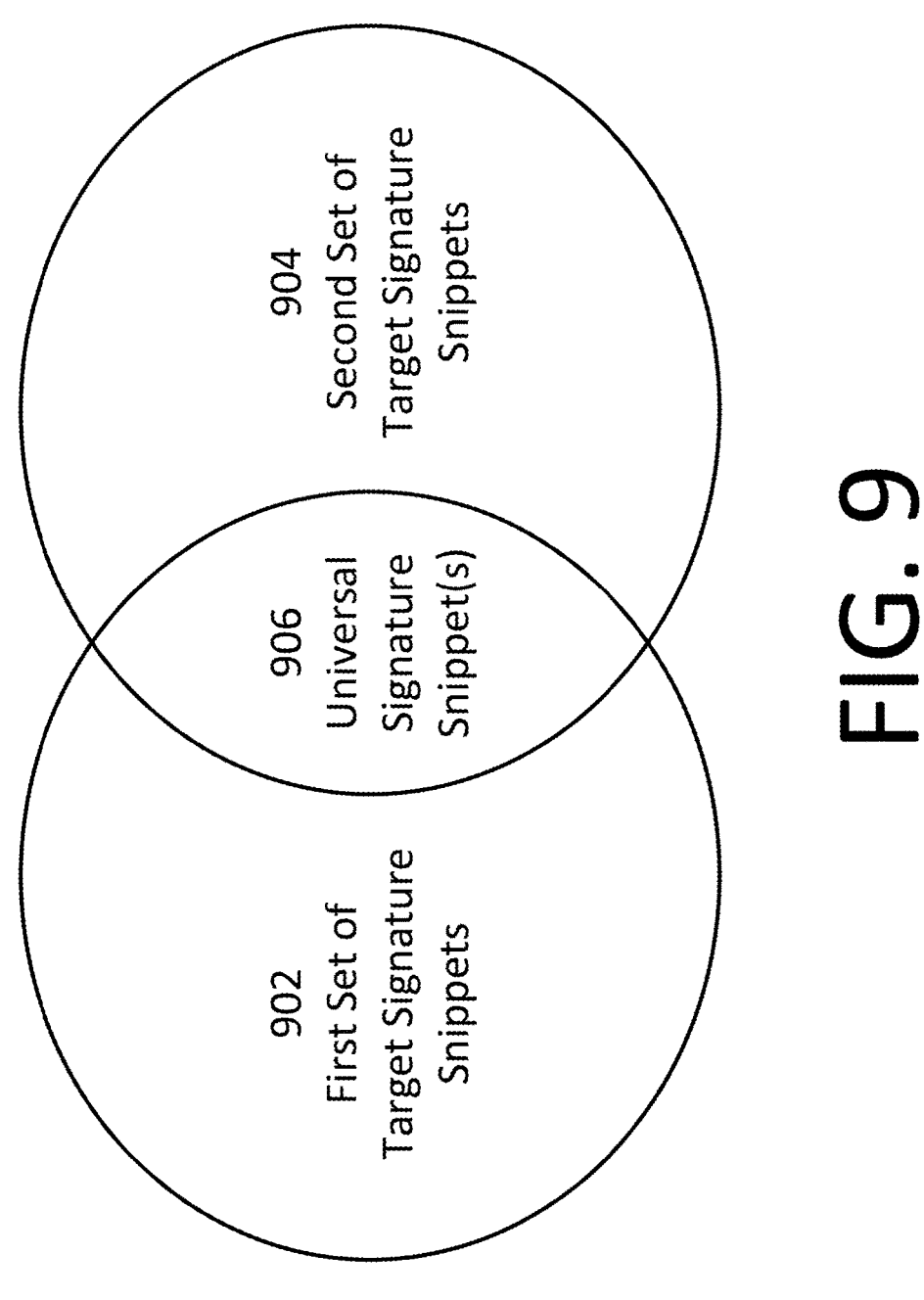
FIG. 9 is a diagram of several sets of target signature snippets according to aspects of the disclosure.

For example, FIG. 9 illustrates a diagram 900 of several sets of target signature snippets identified from several target organisms (for example, the first group of coronaviruses discussed above) according to an example. The diagram 900 includes a first set of target signature snippets 902, a second set of target signature snippets 904, and one or more universal target signature snippets 906 representing the mathematical intersection of the two sets of snippets 902, 904. The diagram 900 includes two sets of target signature snippets for purposes of explanation, but in other examples, the principles discussed herein may be applicable to any other plural number of sets of target signature snippets. Continuing with the example above, if a first group of target coronaviruses includes two coronaviruses, then the two sets of target signature snippets 902, 904 may be considered the set of target signature snippets for each of those two coronaviruses.

The first set of target signature snippets 902 may be identified from a first organism (such as the SARS-CoV-2 virus). For example, the first set of target signature snippets 902 may be identified at act 350 of the process 300, or at acts 650 and/or 660 of the process 600, by analyzing a sequence of the first organism. The second set of target signature snippets 904 may be identified from a second organism (such as a genetic variant of the SARS-CoV-2 virus). For example, the first set of target signature snippets 902 may be identified at a subsequent execution of act 350 of the process 300, or at acts 650 and/or 660 of the process 600, by analyzing a sequence of the second organism.

One or more target signature snippets may be in both the first set of target signature snippets 902 and the second set of target signature snippets 904. In FIG. 9, these universal target signature snippets 906 are represented by the mathematical intersection of the sets 902, 904. The universal target signature snippets 906 are "universal" inasmuch as they are present in all of the sets 902, 904 of the diagram 900.

In some examples, a set of universal target signature snippets may be identified for a group of organisms, such as a group of target coronaviruses. The set of universal target signature snippets may be significantly smaller than the combination of all of the sets of target signature snippets from which the universal target signature snippets is derived. For example, in FIG. 9, a size of the universal target signature snippets 906 will be less than the combination of a size of the first set of target signature snippets 902 and the second set of target signature snippets 904 as long as the sets 902, 904 include at least one non-common target signature snippet, because the at least one non-common target signature snippet is excluded from the universal target signature snippets 906.

It may be advantageous to identify a set of universal target signature snippets and use the set of universal target signature snippets to determine if the universal target signature snippets are present in at least one test sequence (for example, as discussed above at acts 420 and 720). In one non-limiting example, the set of universal target signature snippets may be identified from sets of target signature snippets derived from similar organisms. For example, a set of target signature snippets may be derived from the SARS-CoV-2 virus and from each of several genetic variants of the SARS-CoV-2 virus. A set of universal target signature snippets may be identified from these sets. A resultant set of universal targets signature snippets may be applied to one or more test sequence to predict, for example, whether a given test sequence is derived from the SARS-CoV-2 virus or the genetic variants thereof.

This may be advantageous at least because, as discussed above, a size of a set of universal target signature snippets may be significantly smaller than a size of the combination of sets of target signature snippets used to create the set of universal target signature snippets. Thus, analyzing the at least one test sequence may be significantly faster at least because there are fewer target signature snippets against which to compare the at least one test sequence. Furthermore, a number of false positives may be reduced at least because it is less likely that a target signature snippet is spurious if it is present in every set of target signature snippets. By contrast, it may be more likely that a target signature snippet appearing in the sequence of only one target organism is spurious and likely to yield a false positive. In addition to identifying a set of universal signature snippets, it may be advantageous to filter the set to identify only those universal signatures evidencing low homology with respect to a background sequence to further reduce false positives.

A universal signature, including a low-homology universal signature, may be used in various implementations. For example, a universal signature may be used as a physical probe in analyzing samples for the presence of a gene of interest. For example, a universal signature may be used as a primer in a polymerase chain reaction (PCR) process to "instruct" the polymerase as to which gene to bind to (for example, a certain coronavirus gene). The PCR process may then be executed to amplify, in a sample, a gene of interest indicated by the universal signature. In various examples, the universal signature advantageously amplifies the gene of interest without amplifying other genes, such as genes from a pathogen that is not a pathogen of interest. For example, if a pathogen of interest is the SARS-CoV-2 coronavirus, the universal signature may amplify the SARS-CoV-2 coronavirus without amplifying other coronaviruses which are not of interest. The sample containing the amplified gene of interest may then be used in subsequent analyses.

Figure 10:
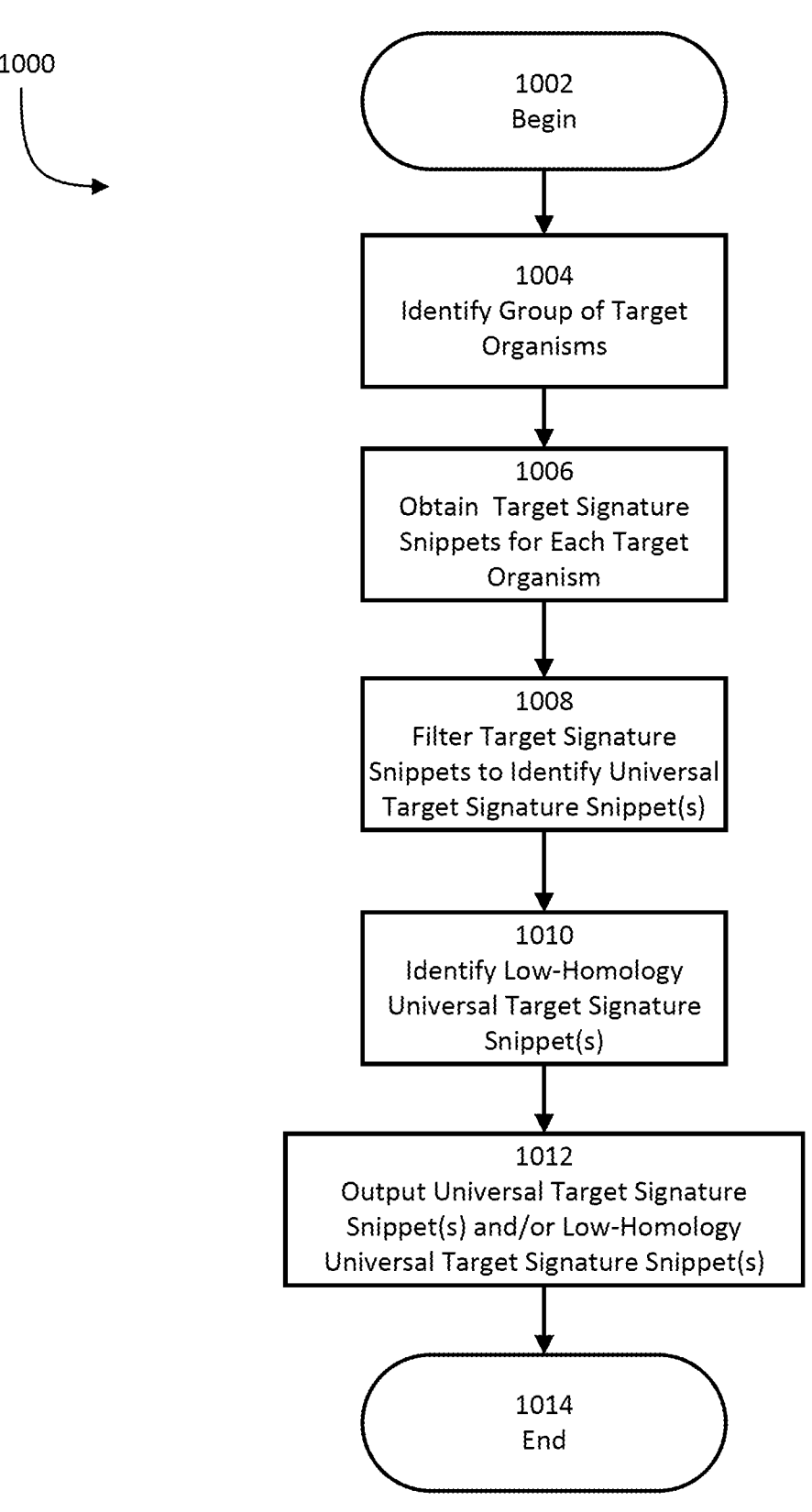
FIG. 10 is a flow diagram of one example of a process of filtering signature snippets according to aspects of the disclosure.

FIG. 10 illustrates a process 1000 of filtering signature snippets according to an example. The process 1000 may be executed, for example, by the processor 130, the processor 530, a combination of both, or another computing device or devices. For purposes of explanation, a description of the process 1000 is provided with respect to the processor 530 and other aspects of the system 500.

At act 1002, the process 1000 begins.

At act 1004, the processor 530 identifies a group of target organisms for which to identify a set of universal target signature snippets. In some examples, the group of target organisms may be identified by a user. Continuing with the example above, the group of target organisms may include the first group of coronaviruses, which may include malicious coronaviruses (as opposed to benign or neutral coronaviruses). For example, a user may identify the SARS-CoV-2 virus and genetic variants thereof as the group of target organisms. It is to be appreciated that target "organisms" are specified for purposes of example only, and that the principles of the disclosure are more broadly applicable to "targets" generally; in some examples, the process 1000 may be executed with respect to synthetic sequences in addition to, or in lieu of, organism sequences. That is, the group of targets identified at act 1004 may include target organism sequences, target synthetic sequences, or a combination of both.

At act 1006, the processor 530 obtains a set of target signature snippets for each target organism of the group of target organisms. The group of target organisms may include organisms for which a set of target signature snippets has been identified and stored in a database. For example, any of the signature snippet databases 520a-c may store sets of target signature snippets for the SARS-CoV-2 virus and genetic variants thereof. Thus, the processor 530 may obtain the sets of target signature snippets by requesting the sets of target signature snippets for each target organism from a corresponding one or more of the signature snippet databases 520a-520c. In another example, a set of target signature snippets may not have yet been identified for at least one of the target organisms. For each such target organism, the processor 530 and/or the processor 130 may execute the process 300 and/or the process 600 to identify a set of target signature snippets for the target organism.

As discussed above with respect to the processes 300, 600, the target signature snippets identified for a given organism may vary based on which sequences are selected as a background (for example, which sequences are identified as benign at act 320). In various examples, in executing the processes 300, 600, the processor 130, 530 may identify particular groups of organisms to act as a background. Continuing with the example above, consider a set of coronaviruses (for example, all known coronaviruses). Each coronavirus in the set of coronaviruses may be classified (for example, by a user) as belonging to either a first group of targets (for example, malicious coronaviruses such as SARS-CoV-2 and genetic variants thereof), a second group of non-targets (for example, benign coronaviruses), or a third group of neutrals (for example, SARS-CoV-1).

Using the process 300 as an example, the plurality of benign snippets identified at act 320 may be derived from the second group of non-targets. The plurality of candidate signature snippets identified at act 330 may be derived from the first group of targets. The third group of neutrals may not be used in executing the process 300. Thus, target signature snippets identified at act 350 may be able to classify a given coronavirus sample as belonging to the target group or the non-target group. The target signature snippets may or may not identify coronaviruses classified into the neutral group but, as discussed above, it may be unimportant whether or not coronaviruses in the neutral group are identified.

At act 1008, the processor 530 filters the sets of target signature snippets obtained at act 1006 to identify a set of universal target signature snippets. Universal target signature snippets may include those target signature snippets that are present in every one of the sets of target signature snippets. In one example, the processor 530 analyzes each target signature snippet in every set of target signature snippets obtained at act 1006 to determine whether the respective target signature snippet is present in every set of target signature snippets obtained at act 1006. Determining whether the respective target signature snippet is present in each set of target signature snippets may be substantially similar to the process 400, where the "malicious snippet" of act 420 is the respective target signature snippet and the "at least one test sequence" of act 420 includes all of the target signature snippets in every set of target signature snippets obtained at act 1006. In another example, determining whether the respective target signature snippet is present in each set of target signature snippets may include executing a matcher algorithm, such as an elementwise matcher algorithm, with each target signature snippet against every other target signature snippet in every set of target signature snippets obtained at act 1006. In still other examples, other methods may be implemented to determine whether a target signature snippet is present in every set of target signature snippets obtained at act 1006.

In some examples, if a target signature snippet is not present in every set of target signature snippets obtained at act 1006, then the target signature snippet is not added to the set of universal target signature snippets. In other examples, a target signature snippet is added to the set of universal target signature snippets provided that the target signature snippet is present in at least a threshold amount of the sets of target signature snippets obtained at act 1006. For example, a threshold amount may be a particular number of sets of target signature snippets, or a particular threshold percentage of the sets of target signature snippets obtained at act 1006. The threshold amount may be static or variable. For example, the threshold amount may vary as the number of sets of target signature snippets obtained at act 1006 varies.

In some examples, act 1008 may include determining whether the set of universal target signature snippets includes at least a threshold number of universal target signature snippets. If the set does not include at least the threshold number of universal target signature snippets (for example, if no, or not enough, universal target signature snippets exist), then the process 1000 may continue to act 1014 and end. In other examples, a notification may be provided to a user, but the process 1000 may continue, subject to the user providing contrary instructions. In still other examples, the conditions for a target signature snippet to be added to the set of universal target signature may be relaxed, automatically and/or as directed by a user, until the set of universal target signature snippets includes a threshold number of snippets.

At act 1010, the processor 530 identifies low-homology universal target signature snippets from the set of universal target signature snippets identified at act 1008. Homology may refer to a degree of similarity between a universal target signature snippet and one or more background sequences, such as the plurality of benign snippets identified at act 320 and/or stored in either or both of the benign snippet databases 110, 510. It may be advantageous to identify low-homology universal target signature snippets from the set of universal target signature snippets—that is, those of the universal target signature snippets that are not very similar to the one or more background sequences—because such significantly unique target signature snippets are less likely to result in false positives where a test sequence differs slightly from the background sequence(s).

A degree of homology may be determined by executing an algorithm to determine a degree of similarity between biological sequences, such as a basic local alignment search tool (BLAST) algorithm. An output of such an algorithm may be expressed as, or used to determine, homology parameters such as a percentage of homology between the biological sequences, a number of shared primers, and so forth. Act 1010 may include the processor 530 identifying those of the universal target signature snippets that have homology parameters meeting certain criteria, such as being within certain thresholds. For example, low-homology criteria may include not having greater than 80% homology and sharing one or more primers with the one or more background sequences. That is, in this example, a universal target signature snippet may be rejected as having a homology that is too high with respect to the one or more background sequences if the universal target signature snippet shares more than 80% and one or more primers with the one or more background sequences. Accordingly, at act 1010, the processor 530 filters the set of universal target signature snippets to identify a smaller (or equal-sized) set of low-homology universal target signature snippets.

At act 1012, the processor 530 outputs the set of low-homology universal target signature snippets. In some examples, the processor 530 may also output the set of universal target signature snippets. For example, the set of low-homology universal target signature snippets (and/or the set of universal target signature snippets) may be output to, and stored in, any of the databases 140, 520a-520c. The set(s) may subsequently be implemented in analysis of one or more test sequences, for example, as discussed above with respect to the processes 400, 700 (or, as discussed below, the process 1100). That is, test sequences may be analyzed to determine whether the universal target signature snippets and/or low-homology universal target signature snippets are present in the test sequence and, if so, determine that the test sequence may be derived from a target organism (or synthetic sequence).

At act 1014, the process 1000 ends.

Accordingly, the process 1000 enables multiple sets of target signature snippets for multiple target organisms to be condensed into a single, smaller set. This single, smaller set may be implemented in lieu of the multiple sets of target signature snippets, such as where it may be advantageous to perform faster analysis with fewer false positives.

A non-limiting example is provided for purposes of explanation. In the following example, the process 1000 is executed to identify a set of low-homology universal target signature snippets from multiple sets of target signature snippets. Each set of target signature snippets may be capable of identifying a respective target coronavirus, such as SARS-CoV-2 or genetic variants thereof. All of the sets together may be capable of identifying any known coronavirus classified as a target, as distinguished from a non-target or neutral coronavirus.

At act 1004, a group of target organisms is identified. As explained above, this group may include target coronaviruses. These target coronaviruses may be malicious coronaviruses. For example, the target coronaviruses may include SARS-CoV-2 and genetic variants thereof.

At act 1006, target signature snippets are obtained for each target organism. At least one of these target signature snippets may have already been previously obtained and stored in a database (for example, the malicious signature database 140), in which case act 1006 includes obtaining those target signature snippets from the database. Additionally, at least one of these target signature snippets may not have already been obtained, in which case a process (for example, the process 300 or 600) may be executed to obtain the target signature snippets. The process 1000 may proceed to act 1008 once all of the target signature snippets are obtained.

As discussed above, a particular background may be selected in identifying the target signature snippets. For example, where particular coronaviruses are being targeted (for example, SARS-CoV-2 and genetic variants thereof), the background may be, or include, all other coronaviruses, which may be considered benign. In some examples, certain coronaviruses may be classified as neutral, as discussed above.

At act 1008, the target signature snippets are filtered to identify one or more universal target signature snippets. As discussed above, the universal target signature snippets may include those snippets that are universal amongst the target signature snippets for every target organism (or at least a threshold proportion of the target organisms). For example, a universal target signature snippet may be universally present in all of the target coronaviruses, and may be absent in all of the non-target coronaviruses. In examples in which neutrals are identified, it may be irrelevant whether or not the universal target signature snippet is present in the neutrals. Accordingly, at act 1008, a reduced number of high-efficacy signatures may be identified for subsequent classification of test sequences.

At act 1010, low-homology universal target signature snippets are identified from the universal target signature snippets. For example, a BLAST algorithm may be executed to determine a degree of homology between the universal target signature snippets and the background coronaviruses. This may be more computationally feasible than determining a degree of homology between the target signature snippets obtained at act 1006 and the background coronaviruses at least because a size of the universal target signature snippets may be significantly smaller than a size of the combination of the target signature snippets.

If any universal target signature snippet is determined to exhibit a degree of homology that is sufficiently significant (for example, exhibiting at least 80% homology), then the universal target signature snippet may be identified as not being a low-homology universal target signature snippet because the universal target signature snippet is too similar to the background coronaviruses. Such a high-homology snippet may be too similar to the background coronaviruses and thus likely to yield false positives. Conversely, if a universal target signature snippet exhibits a low degree of homology (for example, exhibiting less than 80% homology), then the universal target signature snippet may be identified as a low-homology universal target signature snippet. A low-homology universal target signature snippet may be advantageous at least because, by virtue of the low degree of homology with background coronaviruses, the low-homology universal target signature snippet may be less likely to result in a false positive.

At act 1012, the low-homology universal target signature snippets and/or universal target signature snippets are output. For example, the processor 530 may output the snippets by providing the snippets to a database, such as the malicious signature database 140. As discussed above, the snippets may later be used to classify test sequences. For example, a test sequence of a certain coronavirus may be analyzed using the low-homology universal target signature snippets or universal target signature snippets to determine whether the coronavirus is a target coronavirus or a non-target coronavirus. It may be possible to perform the analysis more quickly than if a larger number of target signature snippets were implemented (for example, using the sets of target signature snippets obtained at act 1006) at least because the filtered snippets are smaller in number, and thus there are fewer signatures against which to compare a sample. Accordingly, examples disclosed herein enable relatively fast, high-efficiency classification of test sequences.

Test sequences (or subportions thereof) to be analyzed for the presence or absence of targets may be received in several ways. In some examples, a complete test sequence or subportions thereof may be stored in a file, and the file may be transmitted to a computing device configured to access the test sequence in the file and classify the test sequence. The test sequence may have been determined by a sequencer, such as a DNA sequencer. As appreciated by one of skill in the art, a sequencer is used to automate a genetic sequencing process by analyzing a sample, determining a genetic sequence of the sample, and outputting a genetic read including the genetic sequence of the sample. The read may be output as a text string, which may be stored in a file, as discussed above.

In some examples, principles of the disclosure may be applied to the output of a sequencer before the sequencer has finished sequencing a sample. For example, a genetic sequence may be analyzed (including, for example, classifying the sequence as a target or non-target) as the sequence is output from the sequencer substantially in real time or near-real time.

Figure 11:
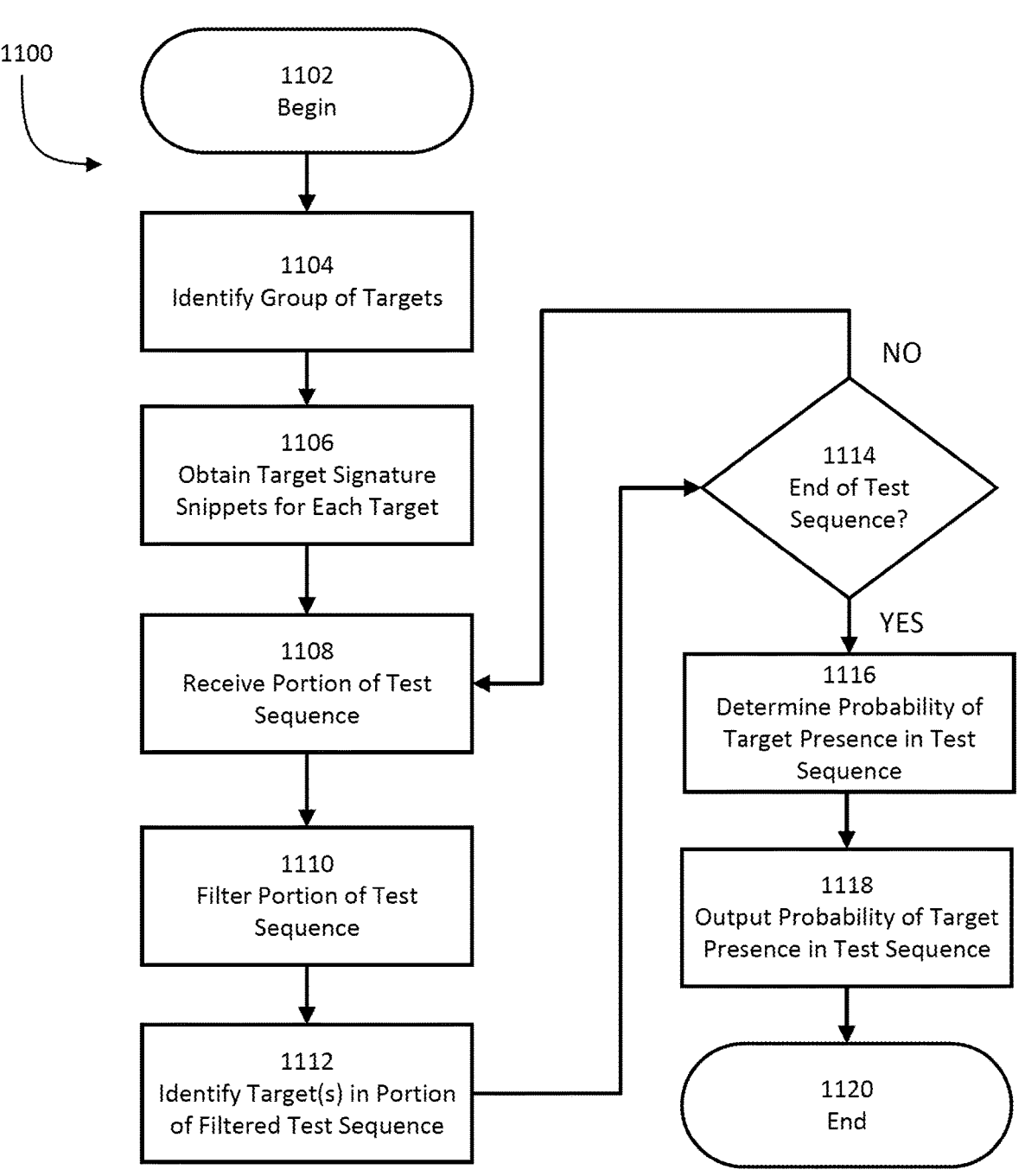
FIG. 11 is a flow diagram of one example of analyzing an output of a sequencer according to an example.

FIG. 11 illustrates a process 1100 of analyzing an output of a sequencer according to an example. In various examples, the process 1100 may be executed by a processor, such as the processors 130, 530. The processor may be a component of the sequencer in some examples. In other examples, the processor may be a component of a device other than the sequencer. For example, the processor may be component of a device that can be communicatively coupled to a sequencer to receive an output of the sequencer in real- or near-real time. In other examples, the processor may be a component of another device.

At act 1102, the process 1100 begins.

At act 1104, a group of targets is identified. For example, a group of organisms to be searched for in a test sequence may be identified. In some examples, the group of targets may be selected by a user. A user may select, for example, a certain group of coronaviruses, such as SARS-CoV-2 and genetic variants thereof.

At act 1106, target signature snippets are obtained for each target identified at act 1104. Target signature snippets may include universal target signature snippets and/or low-homology universal target signature snippets. In some examples, the target signature snippets may include, for example, the snippets identified in acts 350, 650, and 660, discussed above. The target signature snippets may be obtained by accessing a database containing the target signature snippets, such as one of the databases 140, 520a-520c.

At act 1108, a portion of a test sequence is received. The portion of the test sequence may be received in real time or near-real-time from an output of a sequencer. Act 1108 may be executed before the sequencer has finished sequencing a particular sample. It is therefore to be appreciated that the portion of the test sequence received at act 1108 may be only a subportion of a sample's entire genetic sequence that may eventually be provided in totality by the sequencer. Moreover, the sequencer may be analyzing a sample containing multiple organisms each having a respective genetic sequence. Accordingly, act 1108 may include receiving sequence fragments of multiple genetic sequences.

At act 1110, the portion of the test sequence received at act 1108 is filtered. Act 1110 may be executed in parallel with act 1108. That is, certain portions of the test sequence may be filtered at act 1110 while unfiltered portions of the test sequence are received at act 1108. Filtering the portion of the test sequence may include removing low-quality read information from the portion of the test sequence. Low-quality read information may include sequence information that is likely to be inaccurate, that is, information that is unlikely to represent a true genetic sequence of a sample. Such inaccuracies may be introduced by the sequencer incorrectly sequencing the sample. It may be advantageous to filter out low-quality read information at least because the read information may contain errors, and thus may lead to inaccurate classifications.

Filtering the portion of the test sequence may include applying one or more rules to exclude low-quality read information. For example, if a portion of the test sequence includes more than a threshold number of the same nucleobase in a row, the portion of the test sequence may be filtered out, because it is unlikely that the repeated nucleobases accurately represent a genetic sequence. Continuing with this example, the portion of the test sequence may be filtered out if it contains, for example, more than ten instances of cytosine, guanine, adenine, thymine, or a combination of the foregoing, in a row. Thresholds may vary depending on which nucleobase is being considered. For example, the portion of the test sequencer may be filtered out if it contains, for example, more than ten instances of thymine in a row or more than six instances of cytosine in a row. In other examples, other rules may be applied to filter out low-quality read information.

At act 1112, targets are identified in the filtered portion of the test sequence. Act 1112 may be executed in parallel with acts 1108 and/or 1110. That is, additional portions of the test sequence may be received at act 1108 while certain portions of the test sequence may be filtered at act 1110 and further while targets are identified in filtered portions of the test sequence at act 1112. Targets may be identified as discussed above in the processes 400 and 700. For example, a determination may be made as to whether any of the target signature snippets obtained at act 1106 are present in the filtered portion of the test sequence. Multiple targets may be identified in the filtered portion of the test sequence. For example, both the SARS-CoV-2 virus and a genetic variant thereof may be identified in the filtered portion of the test sequence. An indication of a number of times each target has been identified in a portion of a test sequence may be stored, for example, in storage and/or memory accessible to the processor.

At act 1114, a determination is made as to whether the test sequence has ended, or if additional portions remain for analysis. For example, act 1114 may include determining whether a sequencer is still outputting a sequence of a sample. If the sequence has not been completely sequenced and the sequence is thus not at an end (1114 NO), then the process 1110 returns to act 1108. Acts 1108-1112 are repeatedly (and, in some examples, simultaneously) executed until a determination is made that the entire sequence has been analyzed at acts 1108-1112 (1114 YES), at which point the process 1110 continues to act 1116. In some examples, acts 1108-1112 are executed at a rate that is substantially similar to, and in some examples greater than, a rate at which the sequencer outputs the sequence. For example, in an example in which a sequencer outputs a sequence at approximately 4 MB/minute or more, acts 1108-112 may be executed with respect to at least 4 MB of information per minute, such that analysis of a sequence is performed in substantially real time or near-real time with the output of the sequencer.

At act 1116, a determination is made as to a probability of one or more targets being present in the test sequence. As discussed above with respect to act 1112, each portion of the test sequence may be analyzed to determine which targets may be present in the sample based on the portion of the test sequence. In some examples, every target identified at act 1112 is determined to be in the sample by virtue of having been identified at act 1112. In other embodiments, however, a target may be determined to be in a sample only if the target is identified at act 1112 at least a threshold number of times. A single determination that a target is present in a sample at act 1112 may not be definitive when executed on an entire test sequence (as opposed to high-quality snippets of the test sequence isolated after the sequencing is complete), at least because there may be a high probability that the substantially unfiltered test sequence contains errors. Thus, it may be advantageous to determine that a target is present in a sample only if the target is identified at least a threshold number of times in the sample. Furthermore, in some examples, a binary classification (for example, whether a target is present or is not present) may not be determined in some examples. Rather, a non-discrete probability that a given target is present may be determined.

In one example, a target may be determined to be present only if the target is identified at act 1112 at least a threshold number of times. For example, a threshold may be 100 instances of the target being identified in the sample at act 1112. The threshold may vary based on the target. Multiple thresholds may be implemented for each target. For example, a first threshold may correspond to a low likelihood that the target is present in the sample, a second threshold may correspond to a moderate likelihood that the target is present in the sample, and a third threshold may correspond to a high likelihood that the target is present in the sample. Any number of thresholds may be implemented and may vary by target. In some examples, a determination may be made as to a probability that a target is present in the sample, where a greater number of identifications of the target at act 1112 may generally correspond to a greater probability that the target is present in the sample.

At act 1118, a probability of the presence of each target identified at act 1104 is output. A probability for each target may be expressed as, for example, a binary prediction (for example, present or not present), a non-discrete probability (for example, a 98% chance that a target is present), a multi-tiered prediction (for example, a prediction that the target is not present or that there is a low, moderate, or high likelihood that the target is present), and so forth. Probabilities may be expressed differently for different targets, which may vary based on a confidence level that a target is present. For example, if there is less than a 5% chance that a target is present, the output at act 1118 may simply indicate that the target is not present. If there is greater than a 99% chance that a target is present, the output at act 1118 may simply indicate that the target is present. If there is a 5-99% chance that the target is present, the output at act 1118 may indicate the percentage probability that the target is present. In other examples, other formats of outputs are contemplated. Act 1118 may include outputting the probability(ies) to a user, for example, to a user interface accessible to the user. Act 1118 may alternately or additionally include storing information in one or more remote or local databases. In other examples, act 1118 may include outputting the information in additional or different manners.

At act 1120, the process 1100 ends. In various examples discussed above, nucleic-acid sequences may be analyzed, used for target signature snippets, and so forth. In some examples, nucleic-acid sequences may be converted to amino-acid sequences prior to performing analysis, filtering, and so forth. For example, in the process 1000, target signature snippets may be amino-acid signatures, and the remainder of the process 1000 may be performed with respect to amino-acid sequences. Thus, references to sequences in the foregoing description may refer to nucleic-acid sequences, amino-acid sequences, a combination of both, and so forth. Translating nucleic-acid sequences to amino-acid sequences may be performed during, prior to, or after execution of the process 1000. Similarly, in the process 1100, the test sequence received at act 1108 may be converted to an amino-acid sequence prior to performing the remainder of the process 1100.

Figure 8:
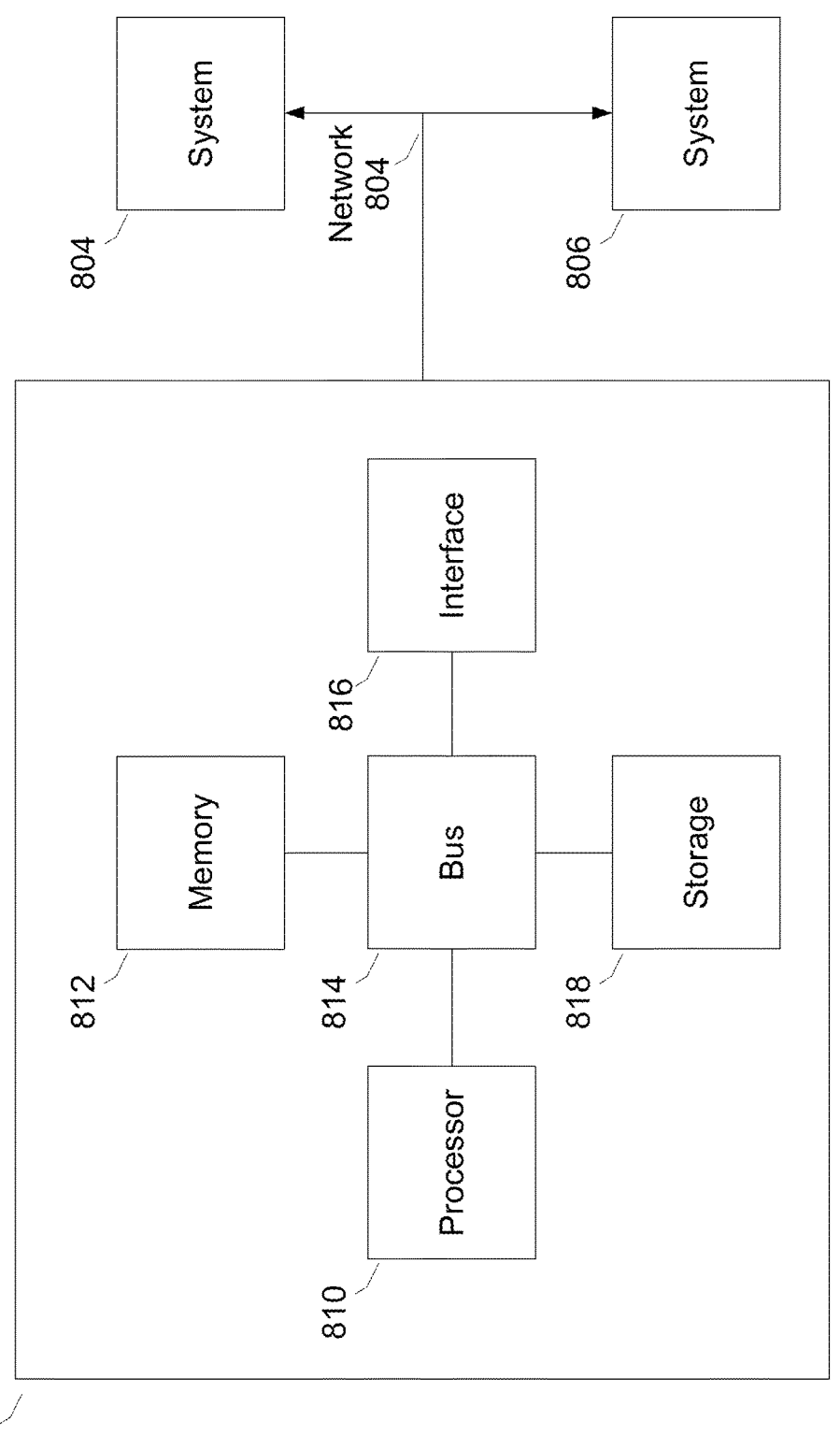
FIG. 8 is a block diagram of one example of a computer system on which aspects and embodiments of the present disclosure may be implemented.

FIG. 8 is a block diagram of a distributed computer system 800, in which various aspects and functions discussed above may be practiced. The distributed computer system 800 may include, or be coupled to, some or all of the components of the systems 100, 500. The distributed computer system 800 may include one or more computer systems. For example, as illustrated, the distributed computer system 800 includes three computer systems 802, 804 and 806. As shown, the computer systems 802, 804 and 806 are interconnected by, and may exchange data through, a communication network 808. The network 808 may include any communication network through which computer systems may exchange data. To exchange data via the network 808, the computer systems 802, 804, and 806 and the network 808 may use various methods, protocols and standards including, among others, token ring, Ethernet, Wireless Ethernet, Bluetooth, radio signaling, infra-red signaling, TCP/IP, UDP, HTTP, FTP, SNMP, SMS, MMS, SS7, JSON, XML, REST, SOAP, CORBA HOP, RMI, DCOM and Web Services.

According to some embodiments, the functions and operations discussed for producing a three-dimensional synthetic viewpoint can be executed on computer systems 802, 804 and 806 individually and/or in combination. For example, the computer systems 802, 804, and 806 support, for example, participation in a collaborative network. In one alternative, a single computer system (e.g., 802) can generate the three-dimensional synthetic viewpoint. The computer systems 802, 804 and 806 may include personal computing devices such as cellular telephones, smart phones, tablets, "fablets," etc., and may also include desktop computers, laptop computers, etc.

Various aspects and functions in accord with embodiments discussed herein may be implemented as specialized hardware or software executing in one or more computer systems including the computer system 802 shown in FIG. 4. In one embodiment, computer system 802 is a personal computing device specially configured to execute the processes and/or operations discussed above. As depicted, the computer system 802 includes at least one processor 810 (e.g., a single core or a multi-core processor), a memory 812, a bus 814, input/output interfaces (e.g., 816) and storage 818. The processor 810, which may include one or more microprocessors or other types of controllers, can perform a series of instructions that manipulate data. As shown, the processor 810 is connected to other system components, including a memory 812, by an interconnection element (e.g., the bus 814). In some examples, the processor 810 may be, include, or be coupled to either or both of the processors 130, 530. For example, the processor 810 may, alone or in combination with other devices, execute any of the processes 300, 400, 600, 700, 1000, and/or 1100.

The memory 812 and/or storage 818 may be used for storing programs and data during operation of the computer system 802. For example, the memory 812 may be a relatively high performance, volatile, random access memory such as a dynamic random-access memory (DRAM) or static memory (SRAM). In addition, the memory 812 may include any device for storing data, such as a disk drive or other non-volatile storage device, such as flash memory, solid state, or phase-change memory (PCM). In further embodiments, the functions and operations discussed with respect to generating and/or rendering synthetic three-dimensional views can be embodied in an application that is executed on the computer system 802 from the memory 812 and/or the storage 818. For example, the application can be made available through an "app store" for download and/or purchase. Once installed or made available for execution, computer system 802 can be specially configured to execute the functions associated with producing synthetic three-dimensional views.

Computer system 802 also includes one or more interfaces 816 such as input devices (e.g., camera for capturing images), output devices and combination input/output devices. The interfaces 816 may receive input, provide output, or both. The storage 818 may include a computer-readable and computer-writeable nonvolatile storage medium in which instructions are stored that define a program to be executed by the processor. The storage system 818 also may include information that is recorded, on or in, the medium, and this information may be processed by the application. A medium that can be used with various embodiments may include, for example, optical disk, magnetic disk or flash memory, SSD, among others. Further, aspects and embodiments are not to a particular memory system or storage system.

In some embodiments, the computer system 802 may include an operating system that manages at least a portion of the hardware components (e.g., input/output devices, touch screens, cameras, etc.) included in computer system 802. One or more processors or controllers, such as processor 810, may execute an operating system which may be, among others, a Windows-based operating system (e.g., Windows NT, ME, XP, Vista, 7, 8, or RT) available from the Microsoft Corporation, an operating system available from Apple Computer (e.g., MAC OS, including System X), one of many Linux-based operating system distributions (for example, the Enterprise Linux operating system available from Red Hat Inc.), a Solaris operating system available from Oracle Corporation, or a UNIX operating systems available from various sources. Many other operating systems may be used, including operating systems designed for personal computing devices (e.g., iOS, Android, etc.) and embodiments are not limited to any particular operating system.

The processor and operating system together define a computing platform on which applications (e.g., "apps" available from an "app store") may be executed. Additionally, various functions for generating and manipulating images may be implemented in a non-programmed environment (for example, documents created in HTML, XML or other format that, when viewed in a window of a browser program, render aspects of a graphical-user interface or perform other functions). Further, various embodiments in accord with aspects of the present disclosure may be implemented as programmed or non-programmed components, or any combination thereof. Various embodiments may be implemented in part as MATLAB functions, scripts, and/or batch jobs. Thus, the disclosure is not limited to a specific programming language and any suitable programming language could also be used.

Although the computer system 802 is shown by way of example as one type of computer system upon which various functions for producing three-dimensional synthetic views may be practiced, aspects and embodiments are not limited to being implemented on the computer system, shown in FIG. 8. Various aspects and functions may be practiced on one or more computers or similar devices having different architectures or components than that shown in FIG. 8.

Examples provided herein enable analysis of genetic sequences. In some examples provided above, a genetic sequence may be derived from an organism. However, it is to be appreciated that principles discussed provided above are not limited to genetic sequences derived from organisms, and may be implemented in connection with other sequences, such as synthetic sequences.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only, and the scope of the disclosure should be determined from proper construction of the appended claims, and their equivalents.

What is claimed is:

1. A method of analyzing an output of a sequencer in real time, the method comprising:

identifying, by one or more processors, a group of genetic targets, each genetic target being a target organism to be detected in a sample;

determining, by the one or more processors, a plurality of sets of one or more target signature snippets responsive to identifying the group of genetic targets, each set of one or more target signature snippet being derived from a genetic sequence of a respective genetic target of the group of genetic targets, wherein each of the plurality of sets of one or more target signature snippets (i) having previously been classified as corresponding to a respective genetic target of the group of genetic targets, (ii) 1 being derived from a genetic sequence of the respective genetic target, and (iii) do not correspond to snippets derived from a plurality of non-target organism sequences;

filtering, by the one or more processors, the plurality of sets of one or more target signature snippets to identify a set of one or more universal target signature snippets, wherein the set of one or more universal target signature snippets consist of one or more target signature snippets that belong to each of the plurality of sets of one or more target signature snippets and which each identify each genetic target of the group of genetic targets;

receiving and analyzing in real time, by the one or more processors, a plurality of portions of a test sequence output by a sequencer sequencing a sample, wherein each of the particular portions are analyzed within milliseconds of being sequenced by the sequencer and the sequencer outputs the particular portions of the test sequence at a rate of at least 4 megabytes per minute;

determining, by the one or more processors and in real time or near-real time with the output of the sequencer sequencing the sample before the sequencer has finished sequencing the sample and at a rate that is equal to or greater than the rate at which the sequencer outputs the particular portions of the test sequence, whether at least one universal target signature snippet of the set of one or more universal target signature snippets is present in at least one portion of the test sequence of the plurality of portions of the test sequence by comparing the test sequence to each of the one or more universal target signature snippets;

determining, by the one or more processors and for each genetic target of the group of genetic targets, a respective probability the respective genetic target is present in the sample based at least on the determination of whether at least one universal target signature snippet of the set of one or more universal target signature snippets is present in the at least one portion of the test sequence of the plurality of portions of the test sequence; and outputting, by the one or more processors, an analysis of the sample, the analysis indicating the respective probability that each genetic target is present in the sample.

2. The method of claim 1, wherein the plurality of portions of the test sequence includes a first portion and a second portion, and wherein the first portion of the test sequence output by the sequencer is received before the second portion of the test sequence is generated by the sequencer.

3. The method of claim 1, further comprising filtering the plurality of portions of the test sequence prior to determining whether at least one universal target signature snippet of the set of one or more universal target signature snippets is present in at least one portion of the test sequence of the plurality of portions of the test sequence.

4. The method of claim 3, wherein filtering the plurality of portions of the test sequence includes removing low-quality portions of the test sequence from the plurality of portions of the test sequence; and wherein low-quality portions of the test sequence include portions of the test sequence having greater than a threshold number of nucleobases repeated in a row.

5. The method of claim 1, further comprising:

producing a physical probe based on at least one universal target signature snippet; and performing a polymerase chain reaction process using a sequence of a universal target signature snippet as a primer to amplify a gene of interest in a sample, wherein the gene of interest includes a genetic target indicated by the universal target signature snippet.

6. The method of claim 1, further comprising determining, for each genetic target of the group of genetic targets, a count value indicative of a number of times that at least one respective universal target signature snippet of a respective set of one or more universal plurality of target signature snippets corresponding to the respective genetic target was determined to be present in the test sequence.

7. The method of claim 6, wherein determining, for each genetic target of the group of genetic targets, a respective probability the respective genetic target is present in the sample is based on a respective count value of the respective genetic target.

8. The method of claim 7, wherein a respective probability the respective genetic target is present in the sample increases as the respective count value of the respective genetic target increases.

9. The method of claim 7, further comprising:

determining whether a respective count value of each respective genetic target exceeds a respective threshold number; and determining that a respective genetic target is present in the sample based on the respective count value exceeding the threshold number.

10. A system for analyzing an output of a sequencer in real time, the system comprising:

a memory;

at least one database configured to store target signature snippets;

at last one processor coupled to the memory and to the at least one database and configured to:

identify a group of genetic targets, each genetic target being a target organism to be detected in a sample;

determine a plurality of sets of one or more target signature snippets responsive to identifying the group of genetic targets, each set of one or more target signature snippet being derived from a genetic sequence of a respective genetic target of the group of genetic targets, wherein each of the plurality of sets of one or more target signature snippets (i) having previously been classified as corresponding to a respective genetic target of the group of genetic targets, (ii) 1 being derived from a genetic sequence of the respective genetic target, and (iii) do not correspond to snippets derived from a plurality of non-target organism sequences;

filter the plurality of sets of one or more target signature snippets to identify a set of one or more universal target signature snippets, wherein the set of one or more universal target signature snippets consist of one or more target signature snippets that belong to each of the plurality of sets of one or more target signature snippets and which each identify each genetic target of the group of genetic targets;

receive and analyze in real time a plurality of portions of a test sequence output by a sequencer sequencing a sample, wherein each of the particular portions are analyzed within milliseconds of being sequenced by the sequencer and the sequencer outputs the particular portions of the test sequence at a rate of at least 4 megabytes per minute;

determine in real time or near-real time with the output of the sequencer sequencing the sample before the sequencer has finished sequencing the sample and at a rate that is equal to or greater than the rate at which the sequencer outputs the particular portions of the test sequence, whether at least one universal target signature snippet of the set of one or more universal target signature snippets is present in at least one portion of the test sequence of the plurality of portions of the test sequence by comparing the test sequence to each of the one or more universal target signature snippets;

determine, by the one or more processors and for each genetic target of the group of genetic targets, a respective probability the respective genetic target is present in the sample based at least on the determination of whether at least one universal target signature snippet of the set of one or more universal target signature snippets is present in the at least one portion of the test sequence of the plurality of portions of the test sequence; and output an analysis of the sample, the analysis indicating the respective probability that each genetic target is present in the sample.

11. The system of claim 10, wherein the plurality of portions of the test sequence includes a first portion and a second portion, and wherein the first portion of the test sequence output by the sequencer is received before the second portion of the test sequence is generated by the sequencer.

12. The system of claim 11, wherein the snippets derived from the plurality of benign organism sequences are determined from at least 1.5 million base pairs of benign organism sequences.

13. The system of claim 10, wherein the at least one processor is further configured to filter the plurality of portions of the test sequence prior to determining whether at least one universal target signature snippet of the set of one or more universal target signature snippets is present in at least one portion of the test sequence of the plurality of portions of the test sequence.

14. The system of claim 13, wherein filtering the plurality of portions of the test sequence includes removing low-quality portions of the test sequence from the plurality of portions of the test sequence; and wherein low-quality portions of the test sequence include portions of the test sequence having greater than a threshold number of nucleobases repeated in a row.

15. The system of claim 10, wherein the at least one processor is further configured to:

determine a degree of homology between each universal target signature snippet of the set of one or more universal target signature snippets and a plurality of background sequences; and identify, in the set of one or more universal target signature snippets, a set of one or more low-homology universal target signature snippets based on a determination that the degree of homology between each respective universal target signature snippet and the plurality of background sequences is less than 80% homology.

16. The system of claim 10, wherein the at least one processor is further configured to determine, for each genetic target of the group of genetic targets, a count value indicative of a number of times that at least one respective target signature snippet of a respective set of one or more universal target signature snippets corresponding to the respective genetic target was determined to be present in the test sequence.

17. The system of claim 16, wherein determining, for each genetic target of the group of genetic targets, a respective probability the respective genetic target is present in the sample is based on a respective count value of the respective genetic target.

18. The system of claim 17, wherein a respective probability the respective genetic target is present in the sample increases as the respective count value of the respective genetic target increases.

19. The system of claim 17, wherein the at least one processor is further configured to:

determine whether a respective count value of each respective genetic target exceeds a respective threshold number; and determine that a respective genetic target is present in the sample based on the respective count value exceeding the threshold number.

20. A non-transitory computer-readable medium storing thereon sequences of computer-executable instructions for analyzing an output of a sequencer in real time, the sequences of computer-executable instructions including instructions that instruct at least one processor to to:

identify a group of genetic targets, each genetic target being a target organism to be detected in a sample;

determine a plurality of sets of one or more target signature snippets responsive to identifying the group of genetic targets, each set of one or more target signature snippet being derived from a genetic sequence of a respective genetic target of the group of genetic targets, wherein each of the plurality of sets of one or more target signature snippets (i) having previously been classified as corresponding to a respective genetic target of the group of genetic targets, (ii) 1 being derived from a genetic sequence of the respective genetic target, and (iii) do not correspond to snippets derived from a plurality of non-target organism sequences;

filter the plurality of sets of one or more target signature snippets to identify a set of one or more universal target signature snippets, wherein the set of one or more universal target signature snippets consist of one or more target signature snippets that belong to each of the plurality of sets of one or more target signature snippets and which each identify each genetic target of the group of genetic targets;

receive and analyze in real time a plurality of portions of a test sequence output by a sequencer sequencing a sample, wherein each of the particular portions are analyzed within milliseconds of being sequenced by the sequencer and the sequencer outputs the particular portions of the test sequence at a rate of at least 4 megabytes per minute;

determine in real time or near-real time with the output of the sequencer sequencing the sample before the sequencer has finished sequencing the sample and at a rate that is equal to or greater than the rate at which the sequencer outputs the particular portions of the test sequence, whether at least one universal target signature snippet of the set of one or more universal target signature snippets is present in at least one portion of the test sequence of the plurality of portions of the test sequence by comparing the test sequence to each of the one or more universal target signature snippets;

determine, by the one or more processors and for each genetic target of the group of genetic targets, a respective probability the respective genetic target is present in the sample based at least on the determination of whether at least one universal target signature snippet of the set of one or more universal target signature snippets is present in the at least one portion of the test sequence of the plurality of portions of the test sequence; and output an analysis of the sample, the analysis indicating the respective probability that each genetic target is present in the sample.

* * * * *